United States Patent [19]

Cho-Chung et al.

[11] Patent Number: 5,843,916
[45] Date of Patent: Dec. 1, 1998

[54] CYCLIC AMP ANALOGUES, INDIVIDUALLY AND IN PAIRS, TO INHIBIT NEOPLASTIC CELL GROWTH

[75] Inventors: Yoon Sang Cho-Chung, Bethesda, Md.; Bernd Jastorff, Oyten; Hans-Gottfried Genieser, Bremen, both of Germany

[73] Assignee: The United States of America as represented by the Department of Health and Human Services, Washington, D.C.

[21] Appl. No.: 225,097

[22] Filed: Apr. 8, 1994

Related U.S. Application Data

[63] Continuation of Ser. No. 877,523, May 1, 1992, abandoned.
[51] Int. Cl.$^6$ .......................... A61K 31/70; C07H 19/213
[52] U.S. Cl. ............................................ 514/47; 536/26.13
[58] Field of Search ............................ 514/47; 536/26.13

[56] References Cited

U.S. PATENT DOCUMENTS

| | | | |
|---|---|---|---|
| 3,849,397 | 11/1974 | Robins, I et al. ..................... | 536/26.13 |
| 3,948,886 | 4/1976 | Shuman et al. ....................... | 536/26.12 |
| 4,058,659 | 11/1977 | Robins, II et al. ................... | 536/26.13 |
| 4,208,406 | 6/1980 | Lapinet et al. ............................ | 514/47 |

OTHER PUBLICATIONS

Genieser et al.(II), "Derivatives of 1β–D–ribofuranosylbenzimidazole 3', 5'–phosphate That Mimic the Actions of Adenosine 3', 5'–phosphate (cAMP) and Guanosine 3', 5'–phosphate (cGMP),"*Carbohydrate Research,*234, 217–235 (1992).
Kano et al., "The Activation of cAMP–dependent Protein Kinase Is Directly Linked to the Reulation of Osteoblast Proliferation (UMR–106) by Parathyroid Hormone,"*Biochem. Biophys. Res. Comm.,* 177(1), 365–369 (1991).
Yokozaki et al., "Unhydrolyzable Analogues of Adenosine 3:5 –Monophosphate Demonstrating Growth Inhibition and Differentiation in Human Cancer Cells, " *Cancer Research,* 52, 2504–2508 (1992).
Beardsley, "Trends in Cancer Epidemiology; A War Not Won," *Scientific American 270* (1), 130–138 (1994)
Ally et al., "Selective Modulation of Protein Kinase Isozymes by the Site–Selective Analog 8–Chloroadenosine 3', 5'–Cyclic Monophosphate Provides a Biological Means for control of Human Colon Cancer Cell Growth," *Proc. Nat. Acad. Sci. USA,*85, 6319–6322 (Sept. 1988).
Clair et al., "Site–Selective cAMP Analogs Induce Nuclear Translocation of the RII cAMP Receptor Protein in Ha–MuSV–Transformed NIH/ 3T3 Calls," *FEBS* Letters, 224(2), 337–384 (Nov.1987).
Cho–chung et al.(I), "Site–Selective Cyclic AMP Analogs as New Biological Tools in Growth Control, Differentiation, and Proto–oncogene Regulation," *Cancer Invest.,*7(2), 161–177 (1989).

Cho–chung et al.(II),"Role of Site–Selective cAMP Analogs in the Control and Reversal of Malignancy,"*Pharmac. Ther.,* 50, 1–33 (1991).
Cho–chung et al.(III),"Role Cyclic AMP Receptor Proteins in Growth, Differentiation, and Suppression of Malignancey: New Approaches to Therapy, " *Cancer Res.,*50, 7093–7100 (Nov. 1990).
Cho–Chung(II), "Site–Selective 8–Chloro–Cyclic Adenosine 3 ', 5'–Monophosphate as a Biologic Modulator of Cancer: Restoration of Normal Control Mechanisms," *J. Nat'l Cancer Inst.,*81 (13), PP. (July 5, 1989).
Cho–chung et al.(IV), "In Vivo Inhibition of Growth of Two Hormone Dependent Mammary Tumors by Dibutyryl1 Cyclic AMP," *Science,*183, 87–88 (Jan. 1974).
Dostmann et al., "Probing the Cyclic Nucleotide Binding Sites of cAMP–Dependent Protein Kinases I and II with Analogs of Adenosine 3',5'–Cyclic Phosphorothioates, " *J. Biol. Chem.,*265(18), 10484–10491 (1990).
Geniesser et al., "Synthesis of Nucleoside–3', 5'–Cyclic Phosphorothioates by Cyclophosphorylation of Unprotected Nucleosides, " *Tetrahedron Letters,*29(23), 2803–2804 (1988).
Helson et al., "A Rationale for the Treatment of Metastatic Neuroblastoma,"*J. Nat'l Cancer Inst.,*57(3), 727–729 (Sept. 1976).
Holmgren et al., "In Vivo Modulation of Intracellular cAMP and Cell Growth of a Lymphatic Tumour in Mice by Cholera Toxin," *Exp. Cell Res.,*108, 31–39 (1977).
Katsaros et al., "Site–Selective Cyclic AMP Analogs Provide a New Approach in the Conrol of Cancer Cell Growth," *FEBS Letters,*223(1), 97–103 (Oct. 1987).
O'Brian et al., "A Kinetic Study of Interactions of (Rp)–and (Sp)–Adenosine Cyclic 3', 5'–Phosphorothioates with Type II Bovine Cardiac Muscle Adenosine Cyclic 3', 5'–Phosphate Dependent Protein Kinase," *Biochemistry,*21, 4371–4376 (1982).
Ogreid et al.(I), "Activation of Protein Kinase Isozymes by Cyclic Nucleotide Analogs Used Singly or in Combination," *Eur. J. Biochem.,* 150, 219–227 (1985).
Ogreid et al.(I), "Comparison of the Two Classes of Binding Sites (A and B) of Type I and Type II Cyclic–AMP–Dependent Protein Kinases by Using Cyclic Nucleotide Analogs, ", Eur. J. Biochem., 181, 19–31 (1989).
Ogreid et al.(I),"Comparison of the Two Classes of Binding Sites (A and B) of Type I and Type II Cyclic–AMP–Dependent Protein Kinases by Using Cyclic Nucleotide Analogs," *Eur. J. Biochem.,* 181, 19–31 (1989).

(List continued on next page.)

*Primary Examiner*—John Kight, III
*Assistant Examiner*—L. Eric Crane
*Attorney, Agent, or Firm*—Leydig, Voit & Mayer, Ltd.

[57] ABSTRACT

A method of inhibiting the proliferation of cells, particularly cancerous cells, by contacting the cells with a phosphorothioate derivative of a cAMP modified at either or both the C-6 and C-8 positions of the adenine moiety, and pharmaceutical compositions therefor.

37 Claims, 9 Drawing Sheets

OTHER PUBLICATIONS

Cho–Chung et al.(V), "Site–Selective cAMP Analogs are Cytostatic and Differentiating Agents for a Spectrum of Human Cancer Cell Lines: Potential for Application to Chemotherapy," *Proc. of ASCO,* 6, Abstract No. 62 (Mar. 1987).

Prasad, "Differentiation of Neuroblastoma Cells in Culture," *Biol. Rev.,*50, 129–265 (1975).

Rannels et al., "Two Different Intrachain cAMP Binding Sites of cAMP–Dependent Protein Kinases," *J. Biol. Chem., J. Biol, Chem.,*255(15), 7085–7088 (1980).

Robinson–Steiner et al., "Probable Involvement of Both Intrachain cAMP Binding Sites in Activation of Protein Kinase," *J. Biol. Chem.,* 258(2), 1032–1040 (1983).

Tagliaferri et al.(I), "Two Classes of cAMP Analogs Synergistically Inhibit p21 ras Protein Synthesis and Phenotypic Transformation of NIH/3T3 Cells Transfected with Ha–MuSV DNA," *Biochem. Biophys. Res. Comm.,*130(3), 1193–1200 (Aug. 1985).

Tagliaferri et a.(II), "Synergistic Inhibition of Growth of Breast and Colon Human Cancer Cell lines by Site–Selective Cyclic AMP Analogs, "*Cancer Res.,* 48, 1642–1650 (Mar. 1988).

Tagliaferri et al.(III), "Reverse Transformation of Harvey Murine Sarcoma Virus–Transformed NIH/3T3 Cells by Site–Selective Cyclic AMP Analogs,"*J. Biol, Chem., 263* (1), 409–416 (1988)

Tortora et al., "Site–Selective cAMP Analogs at Micromolar Concentrations Induce Growth Arrest and Differentiation of Acute–Promyelocytic, Chronic Myelocytic, and Acute Lymphocytic Human Leukemia Cell Lines," *Blood,*71(1), 230–233 (Jan. 1988).

Tsuji et al., "Neuronal Differentiation of Oat Cell Carcinoma In Vitro by Dibutyryl Cyclic Adenosine 3',5'–Monophosphate,"*Cancer Letters,* 1, 311–318 (1976).

CYCLIC AMP ANALOGUES, INDIVIDUALLY AND IN PAIRS, TO INHIBIT NEOPLASTIC CELL GROWTH

This is a continuation of application Ser. No. 07/877,523 filed on May 1, 1992, now abandoned.

FIELD OF THE INVENTION

The present invention relates to phosphorothioate derivatives of cyclic AMP (cAMP) analogues and their use in the regulation of abnormal cell growth, such as that characteristic of cancer cells.

BACKGROUND OF THE INVENTION

Cyclic adenosine monophosphate (cAMP) is a naturally occurring compound that is present in all cells and tissues, from bacteria to humans. In animal cells, cAMP appears to promote the expression of differentiated (specialized) properties. Well-known examples are the stimulation by cAMP of gluconeogenesis in liver, lipolysis in fat tissues, and water permeability in toad bladder epithelium. The functional development of the mammary gland is another example. The content of cAMP in rat mammary glands shows a diphasic pattern during the gestation cycle. The level of cAMP rises continuously toward the end of pregnancy, and then falls progressively to its lowest value by the 16th day of lactation. Subsequent to the onset of lactation, there is a considerable increase in the metabolic activity of the glands coincident with parturition.

Morphological alterations induced by cAMP in cultured cells in vitro include acinar formation and ultrastructural changes in thyroid cells, elongation and array formation in fibroblasts, development of neurite-like outgrowths in neuroblastoma cells, growth of processes in glioma cells, and pigmentation of melanocytes. The rapid changes in cell morphology are probably mediated through an effect by cAMP in interaction with $Ca^{2+}$ on the cytoskeleton. Among the functional effects of cAMP are induction of specific enzymes, stimulation of collagen synthesis in fibroblasts, and neurotransmitter synthesis in cells of neural origin. It is significant that cAMP-induced differentiation may occur without concomitant inhibition of cell division.

While a role for CAMP in cell differentiation seems to be established, it is much more difficult to define a general function for this nucleotide in the regulation of cell proliferation. The available data are interpreted very differently.

In fibroblasts, a number of studies have shown that treatment which relieves the growth inhibition in quiescent cells, such as serum addition or trypsinization, leads to decreased adenylate cyclase activity and a rapid fall in cAMP before the onset of DNA synthesis, supporting the idea that a drop in cAMP level is the decisive signal triggering cell division. However, conclusive evidence that the reduction in cAMP is causally related to the initial release from the resting state has not been presented. In cultured human fibroblasts when $N^6$, $O^{2'}$-dibutyryl-cAMP (DBcAMP) or methylisobutylxanthine was added to prevent the cAMP drop during the first eight hours after serum addition, the subsequent DNA synthesis was not delayed, whereas these agents were inhibitory when added more than eight hours after serum addition, in mid $G_1$, and in late $G_1$ and S phases of the cell cycle. This indicates that a reduction in cAMP may not be involved as the initial trigger for serum-stimulated DNA synthesis, but it may be a factor at later stages, necessary for further progression toward DNA replication. However, in Balb/3T3 cells ($Ca^{+2}$-deprived) stimulated by serum, there is an increase in cAMP in late $G_1$, suggesting a positive role for cAMP in the control of DNA replication in fibroblasts.

Apparently contradictory data also exist in the study of lymphocytes. Cyclic AMP in low concentrations ($10^{-8}–10^6$ M) triggers DNA synthesis in suspension cultures of rat thymic lymphocytes providing one of the main arguments for a growth-promoting role of cAMP. Experiments on peripheral lymphocytes have yielded data that partly support and partly conflict with these results. For liver cells, there is increasing evidence that cAMP may have a positive effect on growth.

Studies showing growth inhibition by cAMP have tended to use higher concentrations of DBcAMP or the other agents than those studies showing growth stimulation, possibly indicating that the observed growth inhibitory effects are less physiological. It has become increasingly evident that effects seen after addition to biological systems of high concentrations of cAMP or DBcAMP are not necessarily direct effects of cAMP, but may be caused by metabolites, such as 5' AMP, adenosine, or butyrate. Similarly, methylxanthines have effects that probably are not mediated through cAMP. Physiologically, it seems that cAMP has several intracyclic modulatory effects on normal cell growth, although it is quite certainly not the only growth regulator. Probably, various growth factors operate by mechanisms independent of cAMP. In fact, cAMP may not be essential for cell cycle progression per se.

The effect of cAMP observed in malignant cells in culture in many cases constitutes a striking redifferentiation, which amounts to apparent renormalization of a number of properties of the transformed cells, including morphological features, adhesive properties, lectin agglutination, cell movement, biochemical functions, and anchorage-dependent growth.

It is unclear how fundamental this "normalization" is. For example, the tumorigenicity of DBcAMP-treated neuroblastoma cells has been reported to be decreased by Prasad (*Biol. Rev.* 50: 129–165, 1975) but was found to be unaltered in another study by Furmanski et al. (J. Schultz, and H. G. Gratzner, Eds., *The Role of Cyclic Nucleotides in Carcinogenesis*, pp. 239–261. New York and London: Academic Press, 1973). The presence of transformation-associated antigens on the cell surface is not prevented by cAMP. There is considerable variation in the morphological response to cAMP from cell to cell, even among fibroblasts.

Animal experiments have shown that various cAMP derivatives may inhibit tumor growth in vivo (cf. Keller, *Life Sci.* 11: 485–491, 1982; and Cho-Chung et al., *Science* 183: 87–88, 1974). An interesting observation was that one single injection of cholera toxin, which is a potent adenylate cyclase activator, caused an almost complete inhibition of YAC lymphoma cell proliferation for up to four days in mice without noticeable toxic effects on the animals (Holmgren et al., *Exp. Cell Res.* 108: 31–39, 1977). Some of the most striking examples of malignant cell differentiation by cAMP in vitro have been observed in neuroblastoma cultures (Prasad, *Biol. Rev.* 50: 129–165, 1975).

A preliminary clinical study with the phosphodiesterase inhibitor papaverine, included in a combined drug regimen for disseminated neuroblastomas that in most cases were unresponsive to other drugs, has yielded promising results (Helson et al., *J. Natl. Cancer Inst.* 57: 727–729, 1976). Also, human oat cell lung carcinoma cells treated in vitro with DBcAMP have differentiated into neurone-like cells (Tsuji et al., *Cancer Lett.* 1: 311–318, 1976). Another interesting example is the induction of differentiation by DBcAMP of spindle cell sarcoma with multiple metastasis (Williams et al., *Proc. Am. Assoc. Cancer Res.* 23: 142, 1983). In this latter case, the patient was treated with DBcAMP (3–6 mg/kg) intravenously for five hours each day on days 1–9 and again on days 47–56. The tumor size plateaued and even decreased during both infusion periods and increased during intervals off treatment and after cessation of the second treatment. Histology of tumors biopsied on days 2, 14, and 60 showed evidence of differentiation during the DBcAMP infusion.

Because cAMP manifests almost ubiquitous biological effects, the unphysiologically high levels of cellular AMP that would result from prior compounds would disturb many cellular processes nonspecifically, resulting in a masking of a specific function of cAMP, such as growth regulation.

Cyclic AMP in mammalian cells functions via binding to its receptor protein, the regulatory subunit of cAMP-dependent protein kinase. There are at least two distinct isozymes for cAMP-dependent protein kinase, namely, type I and type II protein kinases, having different regulatory subunits (RI and RII, respectively) but an identical catalytic subunit, and differential expression of these isozymes has been shown to be linked to regulation of cell growth and differentiation. Recently, two genes have been identified that code for two different catalytic subunits (Cα, Cβ) of cAMP-dependent protein kinase. However, preferential co-expression of either one of these catalytic subunits with either the type I or the type II regulatory subunit has not been found.

Because a mixture of type I and type II kinase isozymes is present in most tissues, selective modulation of these isozymes in intact cells may be a crucial function of cAMP. All past studies of the cAMP regulation of cell growth employed either a few early known cAMP analogues that require an effective concentration of unphysiologically high millimolar range or agents that raise cellular cAMP to abnormally and continuously high levels. Under these experimental conditions, separate modulation of type I and type II kinase isozymes is not possible, because cAMP at high levels activates both isozymes maximally and equally without discrimination.

Recent studies on extensive cAMP binding kinetics, using purified preparations of protein kinase isozymes in vitro, identified site-selective cAMP analogues that selectively bind to either one of two different binding sites on the cAMP receptor protein. Furthermore, the site-selective analogues in appropriate combinations demonstrate synergism of binding and exhibit specificity toward either type I or type II protein kinase. This unique site-specificity of site-selective cAMP analogues is not mimicked by cAMP itself or by previously studied earlier analogues.

Human breast cancers often regress after hormone therapy, treatment that frequently involves the removal of the ovaries. That cancer regression has been linked to the presence of an estrogen receptor (ER) in the tumor, to the extent that assays designed to measure the receptor are now used extensively to identify patients likely to respond to hormone therapy. However, it has become apparent that the mere presence of ER is not a reliable criterion for the response of mammary tumors to endocrine therapy. While patients with undetectable levels of tumor ER rarely respond to endocrine therapy, only 50–60% of ER-positive human breast tumors regress after hormone treatment. There is, therefore, a need to identify hormone-dependent cancers within the group of ER-positive tumors. The presence of progesterone receptor (PgR) in ER-positive tumors has been reported to improve the prediction of endocrine responsiveness in some studies, but in other studies, PgR did not enhance prediction. The presence of PgR, therefore, does not necessarily improve the predictive value of ER. Additional discriminating factors are clearly required.

Evidence that cAMP receptor protein may represent such a parameter has come from studies in which regression of hormone-dependent mammary tumors followed administration of dibutyryl cyclic AMP, the effect being apparently mediated by cAMP receptor protein. Cyclic AMP receptor protein appears to be a marker of tumor sensitivity to hormonal manipulation as was shown in animal tumors and in a limited number of human breast cancers.

It has been suggested that regulation of the growth of hormone-dependent mammary tumors may depend on the antagonistic action between estrogen and cyclic AMP. Estrogen stimulates, whereas cAMP arrests, the growth of mammary carcinomas induced by 7,12-dimethyl-benz(α) anthracine (DMBA) in rat. During growth arrest of the tumors after either hormone removal via ovariectomy or treatment of the hosts with DBcAMP, estrogen binding decreases whereas cAMP binding and cAMP-dependent protein kinase activity increase in the cytosol and nuclei of the tumor cells. It was further demonstrated that the growth of DMBA-induced mammary tumors is associated with an enhanced expression of a cellular oncogene, c-ras. The p21 transforming protein of the ras gene product was a predominant in vitro translation product of mRNAs of the growing tumors, and a sharp reduction of the translated p21 protein preceded regression of these tumors after either ovariectomy or DBcAMP treatment.

Recent studies on cAMP binding kinetics, using purified preparations of cAMP-dependent protein kinases, identified cAMP analogues that are potent activators of protein kinase and selectively bind to either one of the two different cAMP binding sites of protein kinase (cf. Rannels et al., *J. Biol. Chem.* 255: 7085–7088, 1980). Generally, analogues modified at the C-8 position of the adenine ring preferentially bind to site 1 of the protein kinase, whereas those modified at the C-6 position preferentially bind to site 2 of the protein kinase. Furthermore, the Site 1- and Site 2-selective analogues in combination demonstrate synergism of binding to and activation of protein kinase (Robinson-Steiner et al., *J. Biol. Chem.* 258: 1032–1040, 1983).

Cyclic AMP analogues and derivatives thereof that demonstrate selective binding to the two isoforms of the cAMP receptor proteins provide a means to regulate cell growth, in particular the abnormal cell growth that is characteristic of cancer cells. Such analogues are expected to have utility in chemotherapy. Accordingly, the present invention provides phosphorothioate derivatives of cAMP analogues for use in the regulation of the growth of cells, particularly the abnormal cellular growth associated with cancer and leukemia.

SUMMARY OF THE INVENTION

It is an object of the present invention to provide derivatives of cAMP analogues which offer improvements over cAMP analogues.

It is another object of the present invention to provide compositions, in particular pharmaceutical compositions, comprising such improved derivatives of cAMP analogues.

It is still another object of the present invention to provide a means of regulating abnormal cell growth.

It is yet another object of the present invention to provide a means of inhibiting the growth of cancer cells and leukemic cells.

Another object of the present invention is to provide a means of modulating the cAMP receptor proteins.

Yet another object of the present invention is to provide a method of chemotherapy for the treatment of cancer and leukemia, wherein improved derivatives of cAMP analogues are administered in combination with non-derivatized cAMP analogues.

These and other objects and advantages of this invention, as well as additional inventive features, will become apparent from the description of the present invention provided herein.

The present invention provides phosphorothioate derivatives of cAMP modified at either or both the C-6 and C-8 positions of the adenine moiety, particularly phosphorothioate derivatives of 8-halo-cAMP, and especially the phosphorothioate derivative Rp-8-Cl-cAMPS of 8-Cl-cAMP or 8-chloro-adenosine 3': 5'-monophosphate analogue. Rp-8-Cl-cAMPS contains an exocyclic sulfur substitution in the equatorial (Rp) position of the cyclophosphate ring. 8-Cl-cAMP downregulates the $RI_\alpha$ isoform of the cAMP receptor protein and upregulates the RII β, isoform of the cAMP receptor protein. 8-Cl-cAMP, although highly effective in regulating the growth of cells, such as cancer cells, that are characterized by an abnormally high level of RIα and an abnormally low level of RIIβ, is susceptible to hydrolysis by cAMP-phosphodiesterase (PDE). This hydrolysis could result in the production of 8-Cl-adenosine in tissues, such as tumors, that contain high levels of PDE. The 8-Cl-adenosine is a toxic metabolite. In contrast, Rp-8-Cl-cAMPS is resistant to hydrolysis but requires a higher effective concentration than 8-Cl-cAMP due to a reduced affinity for the cAMP receptor protein. Chemotherapeutic treatments are provided wherein treatment with 8-Cl-cAMP is either combined or alternated with Rp-8-Cl-cAMPS.

In this Figure, the values of $IC_{50}$ (concentration inducing 50% inhibition of cell proliferation) were obtained in reference to the growth of untreated control cells. In the chart, 1 is MCF-7, 2 is T-47D, 3 is ZR-75-1; 4 is MCF-7ras-, 5 is MDA-MB-231, 6 is BT-20, 7is HBL-100, 8 is LS-174T, 9 is WiDr, 10 is HT-29.

FIG. 2 shows the effect of cAMP analogues on the morphology of breast cancer cell lines A and B, T-47D; C and D, HBL-100; E and F, MDA-MB-231; G and H, MCF-7ras; B, D, F, and H, treatment with 8-Cl-cAMP at 50 μM at Day 0 and Day 2; A, C, E, and G, untreated control cells. The photographs were taken on Day 4, ×160.

Figure 3:
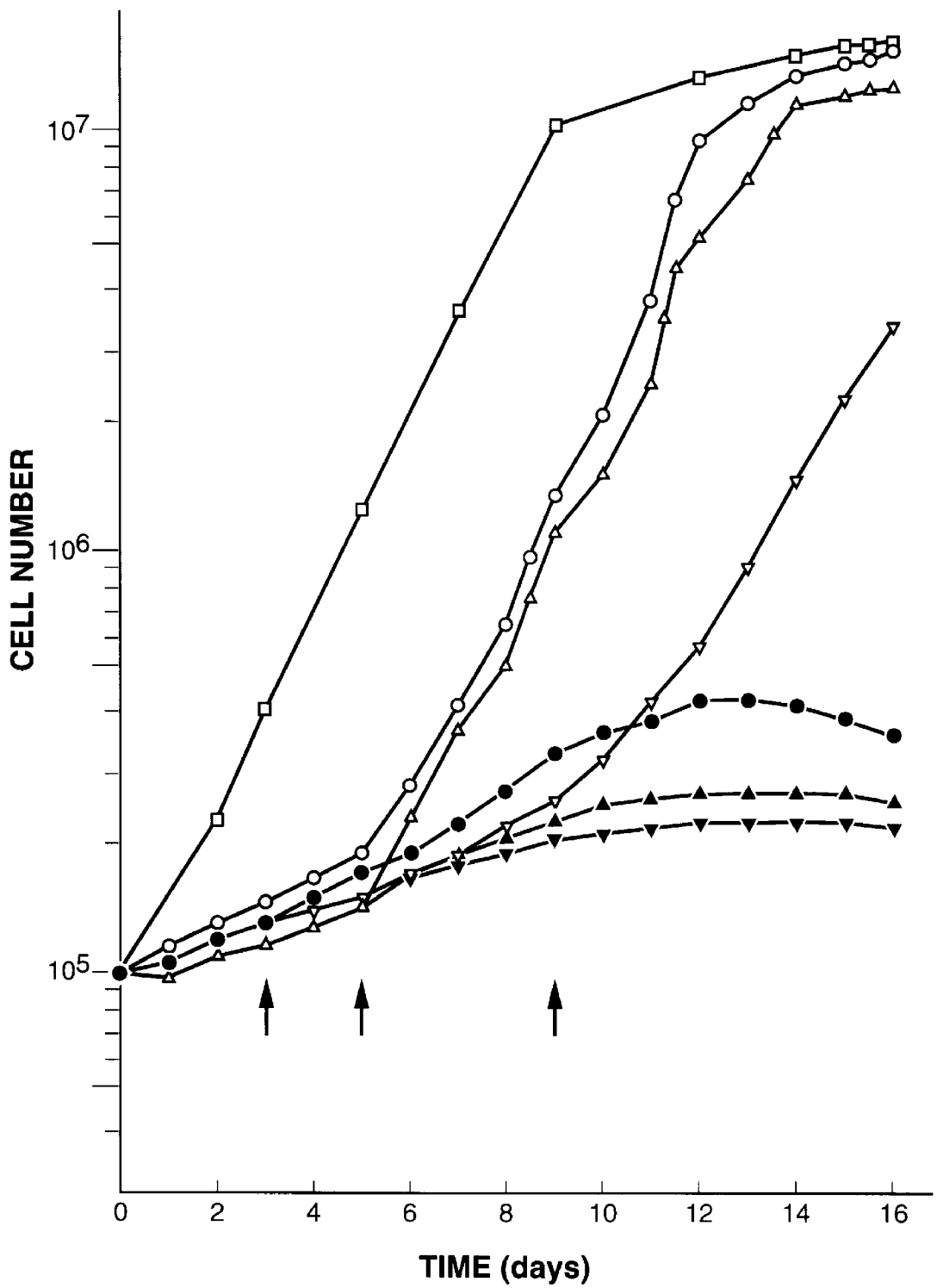

FIG. 3 shows a comparison of the effect of 8-Cl-cAMP and 8-Cl-adenosine on the growth of LS-174T colon cancer line. □, untreated control cell; 0, Δ, ▽ cells treated with 8-Cl-cAMP (10 μM) for 3, 6, and 9 days, respectively; ●,▲, ▼ cells treated with 8-Cl-adenosine (5 μM) for 3, 6, and 9 days, respectively. 1×10⁵ cells/60 mm dish were seeded, and 24 hours later (Day 0), the medium was removed and fresh medium and additives were added then and every 48 hours thereafter. The arrow shows removal of additives. The triplicate cell count for each experimental point never varied by more than 10%.

Figure 4:
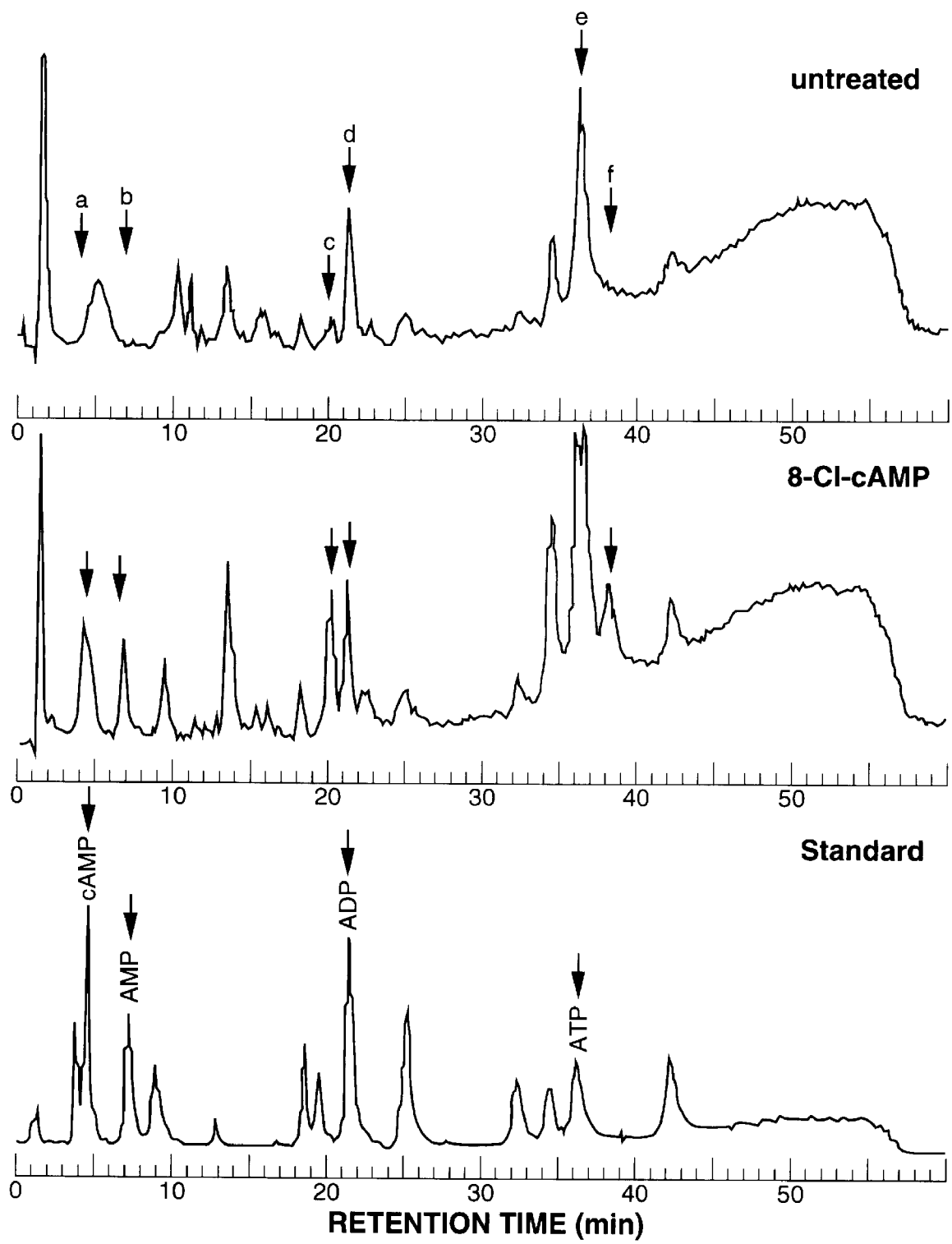

FIG. 4 shows the HPLC analysis of cell extracts after treatment of HT-29 colon cancer cells with 8-Cl-cAMP. HPLC analysis of nucleotides was performed on the cell extracts from cells treated for 72 hours with 8-Cl-cAMP (50 μM) and untreated control cells as described below.

FIG. 5 shows DEAE-Cellulose chromatography of the cytosols from cAMP analogue-treated and untreated LS-174 cells. Cytosols of untreated (A) and treated (for three days with 0.5 μM N⁶-benzyl-cAMP+1μM 8-Cl-cAMP (B) cells were prepared, and the chromatography was performed as below. A, NaCl concentration. Protein kinase activity in the absense (●) and presence (0) of 5 μM cAMP and cAMP binding activity (▲) using 100 μl aliquots of each fraction measured as described below. A unit of enzyme activity of protein kinase was defined as that amount of enzyme that transferred 1 pmol of ³²P from [³²P]ATP to recovered protein in seven minutes at 30° C. in the standard assay. The cAMP binding was expressed as the specific binding calculated by the subtraction of a blank value (the amount of [3H]cAMP bound in the presence of excess nonradioactive cAMP) from the value obtained with radioactive nucleotide alone. The column profile represents one of several similar experiments.

Figure 6:
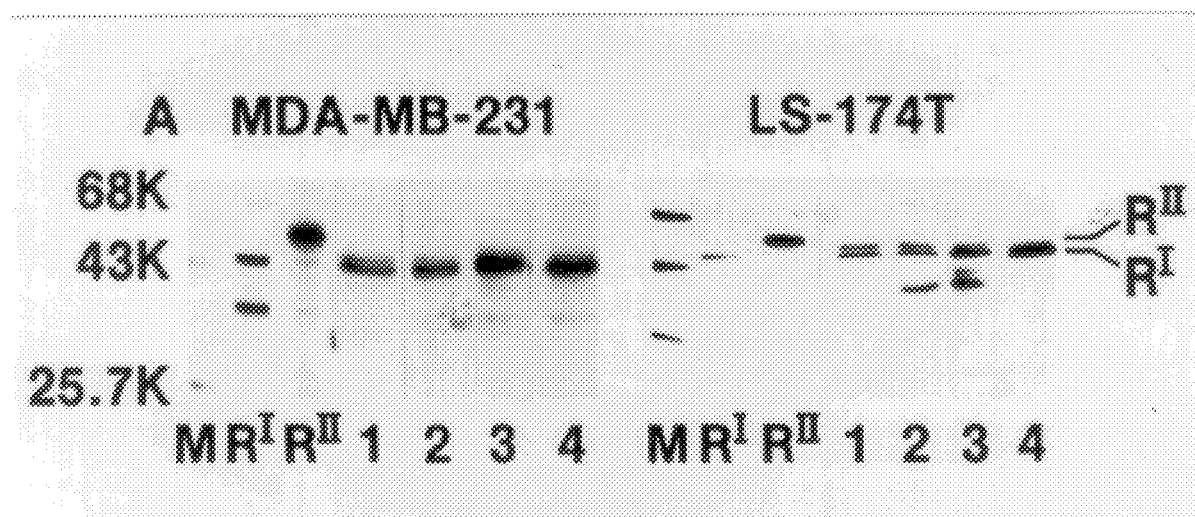

FIG. 6 shows the effects of cAMP analogue treatment on the R', R", receptor levels in breast (MDA-MB-231) and colon (LS-174T) cancer lines. Photoactivated incorporation of 8-N₃[³²P] was performed as described below. R', the 48,000 molecular weight R' cAMP receptor protein; R", the 56,000 molecular weight R" cAMP receptor protein.

In lanes 1, 2, and 3, cells were each treated for 3 days with 8-Cl-cAMP (10 μM), N⁶-benzyl-cAMP (10 μM), and N⁶, O²-dibutyryl-cAMP (1 mM), respectively; lane 4, untreated control cells. M is marker proteins of known molecular weight.

Each lane contained 50 micrograms protein for SDS-PAGE.

Figure 7:
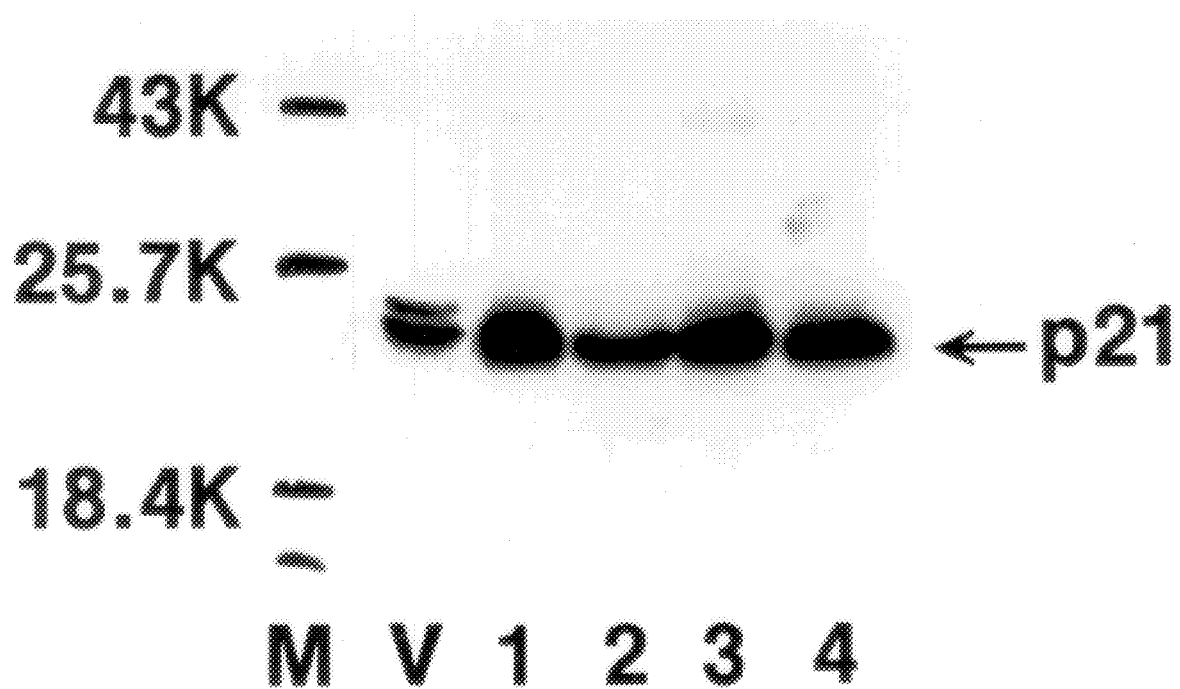

FIG. 7 shows the Western blotting of p21 ras protein in MCF-7 cells before and after cAMP analogue treatment. Western blotting of p21 protein was performed as described below. Lane 1 is the control; lanes 2, 3, and 4, cells treated for three days with 8-Cl-cAMP (10 μM), 8-Cl-adenosine (5 μM), and DBcAMP(500 μM), respectively. V is cell lysate from Ha-MuSV-transformed NIH3T3 clone 13-3B-4. M, marker proteins of known molecular weight.

Each lane contained 100 micrograms of protein for SDS-PAGE.

Figure 8A:
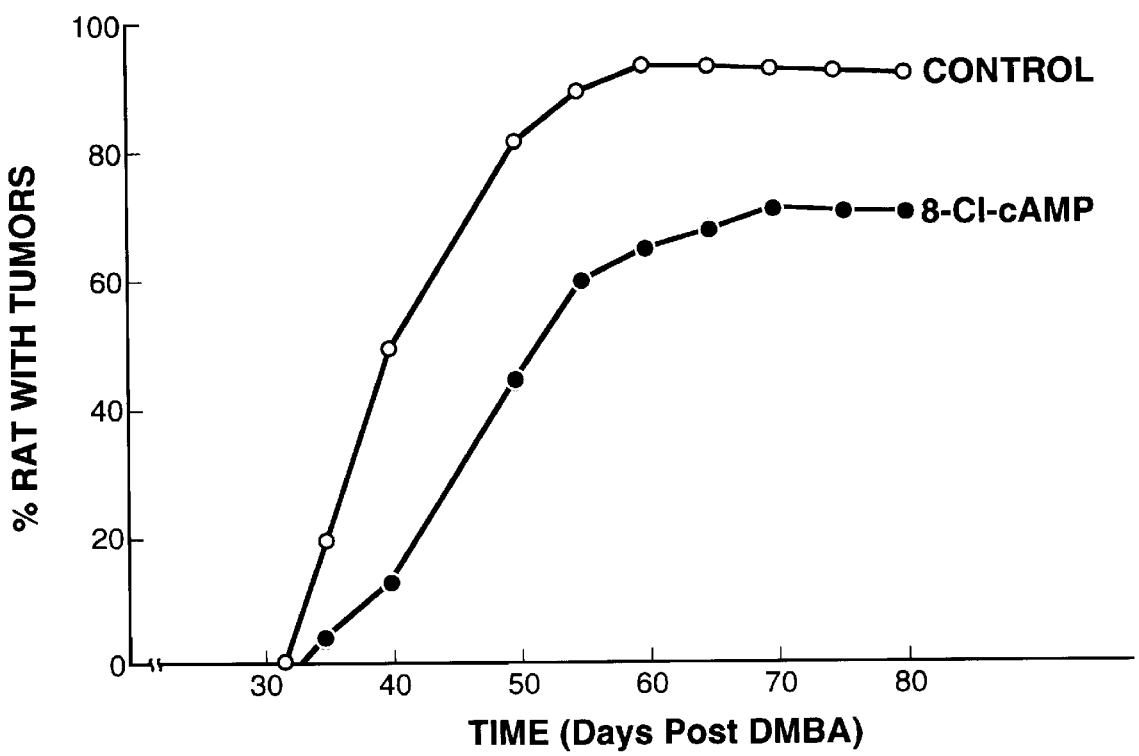
Figure 8B:
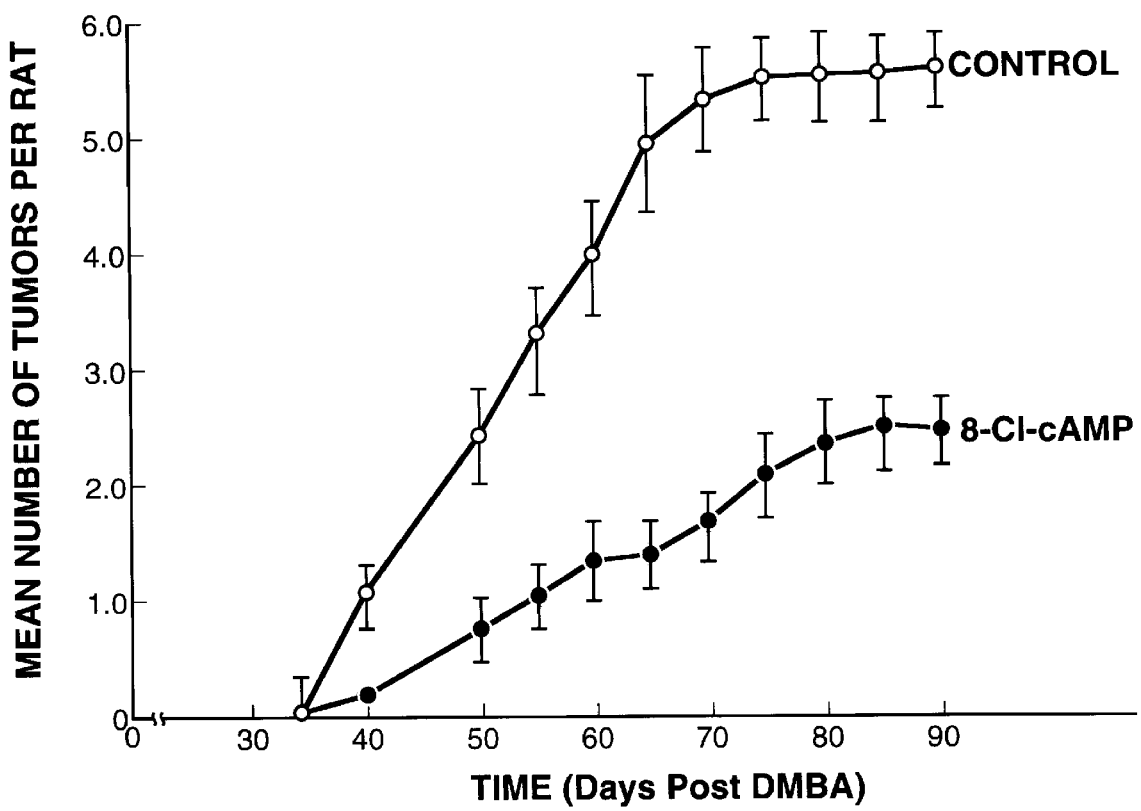

FIG. 8 shows the effect of 8-Cl-AMP pellet on the rate (A) and number (B) of mammary tumor inductions by DMBA.

Figure 9:
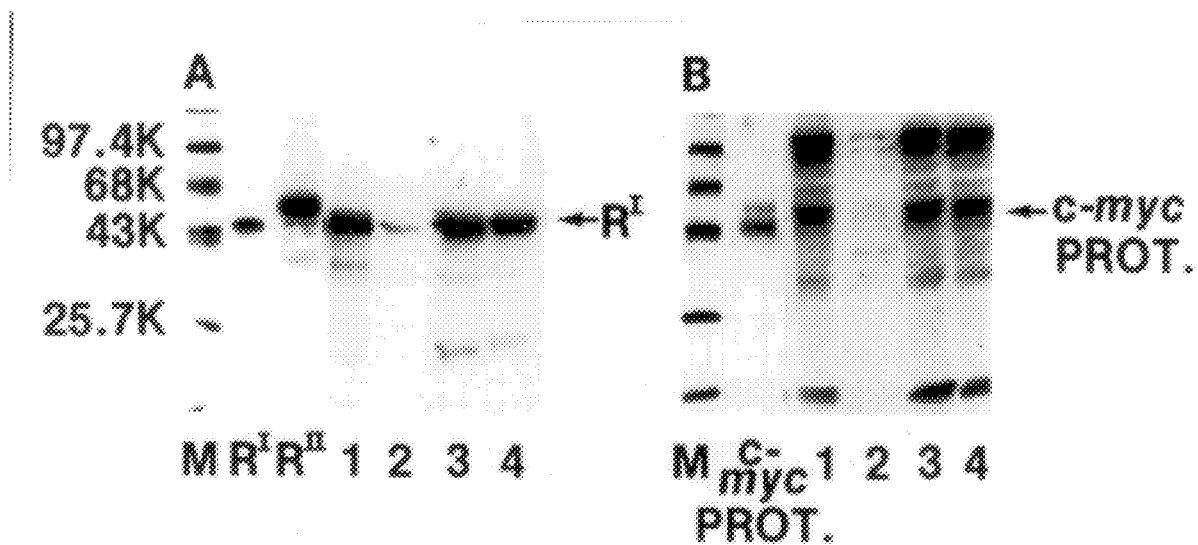

FIG. 9 shows the effect of site-selective cAMP analogue treatment on the levels of CAMP receptor protein and c-myc protein.

Figure 10:
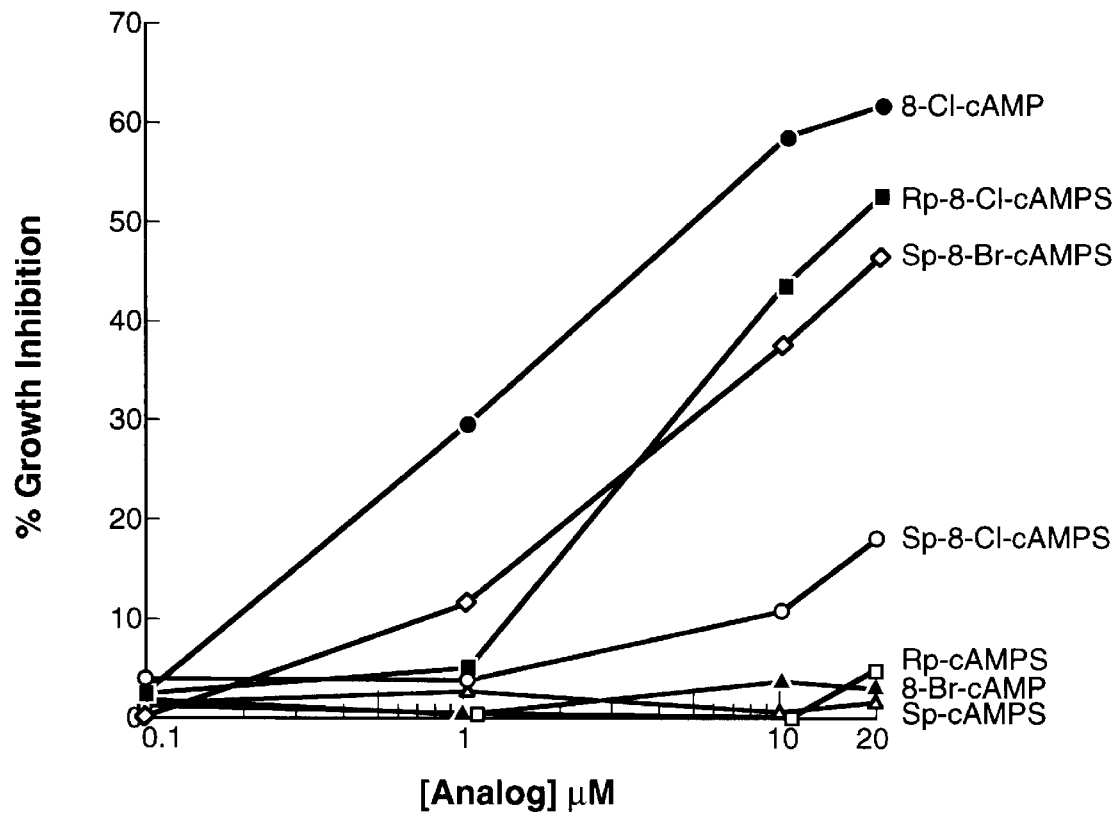

FIG. 10 shows the effect of cAMP analogue concentration on growth inhibition of HL-60 leukemia cells.

Figure 11:
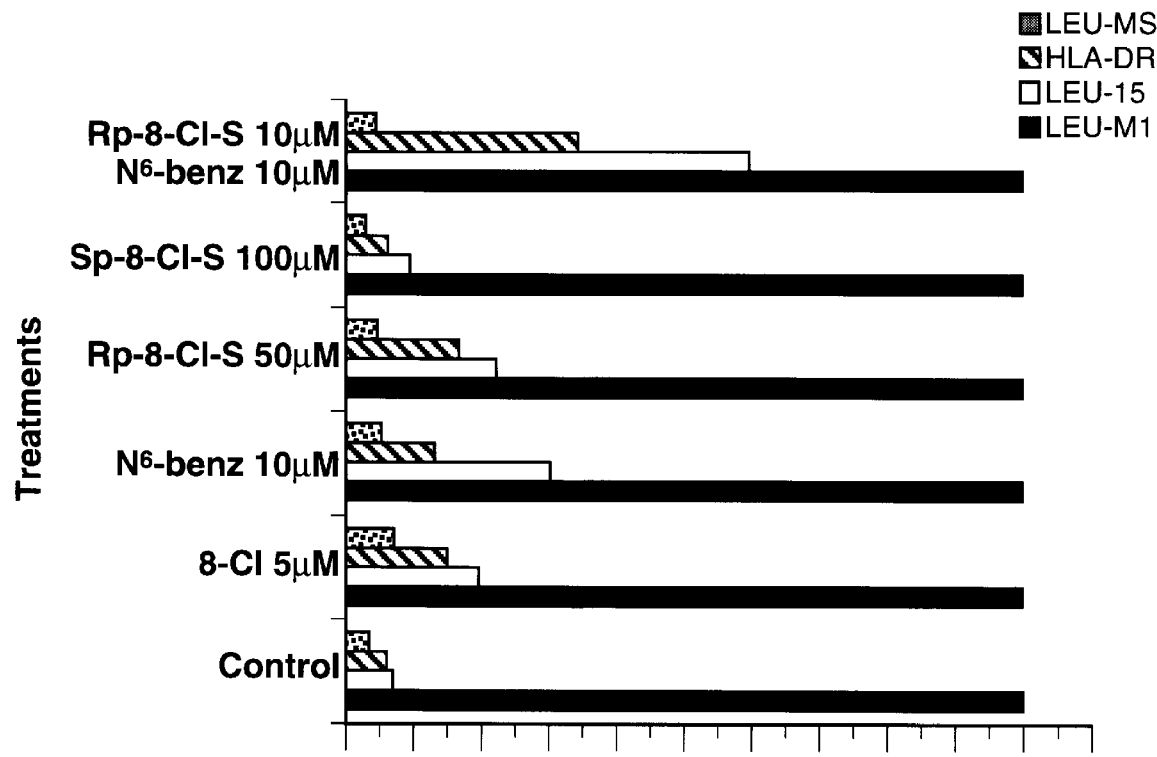

FIG. 11 shows the effect of derivatives of cAMP analogue on the surface marker expression of HL-60 cells.

DETAILED DESCRIPTION OF THE INVENTION

The present invention involves a method of inhibiting the proliferation of cells by contacting the cells with an effective amount of a compound selected from the group consisting of phosphorothioate derivatives of cAMP modified at either or both the C-6 and C-8 positions of the adenine moiety and pharmaceutically acceptable salts thereof. Of particular interest are those phosphorothioate derivatives of 8-halo-cAMP, preferably of 8-Cl-cAMP and 8-Br-cAMP. The most preferred phosphorothioate derivatives are those of Rp-8-Cl-cAMPS and Sp-8-Br-cAMPS, particularly Rp-8-Cl-cAMPS.

The present invention also includes such a method wherein the cells are also contacted with an additional compound selected from the group consisting of 8-Cl-cAMP, $N^6$-benzyl-cAMP, $N^6$-benzoyl-8-methylthio-cAMP, 8-methylthio-cAMP, $N^6$-benzoyl-cAMP, 8-bromo-cAMP, 8-iodo-cAMP, 8-p-chlorophenylthio-cAMP, 8-β-hydroxyethylamino-cAMP, 8-methylamino-cAMP, 8-N,N-dimethylamino-cAMP, $N^6$-phenylcarbamoyl-cAMP, $N^6$-butyryl-cAMP, $N^6$, $O^2$-dibutyryl-cAMP, $N^6$-phenyl-8-p-chlorophenylthio-cAMP, $N^6$,$N^6$-diethyl-8-p-chlorophenylthio-cAMP, 6-piperidino-8-p-chlorophenylthio-cAMP, $N^6$-benzyl-8-benzylthio-cAMP, $N^6$-ethoxycarbonyl-cAMP, $N^6$-n-butyl-8-p-chlorophenylthio-cAMP, pharmaceutically acceptable salts thereof, and mixtures thereof, particularly 8-Cl-cAMP, $N^6$-benzyl-cAMP, and pharmaceutically acceptable salts thereof. The cells may be contacted with these compounds simultaneously, e.g., in a single pharmaceutical composition, or sequentially, e.g., in an alternating sequence.

While the present inventive method is primarily directed to inhibiting cell proliferation, it is also useful in increasing cell differentiation. The present inventive method is useful in connection with the treatment of cells which have more RIα isoform than RIIβ isoform of the cAMP receptor protein, such as cancerous cells, and leukemic cells. The present inventive method is also useful in antagonizing cAMP-dependent protein kinases in vivo.

The present invention is also concerned with compositions, particularly pharmaceutical compositions, which include the compounds useful in the practice of the present inventive method, as well as chemotherapeutic methods for the treatment of mammals using such pharmaceutical compositions. The present inventive method and composition are particularly useful in the treatment of humans.

The compounds of the present invention have been found to be active against a variety of cancer cells. The growth-regulating activity of the compounds and compositions of the present invention were studied using the cyclic nucleotide effector mechanisms involved in cAMP-mediated processes using a test to establish whether or not the cAMP receptor protein is the mediator of the response, and the compounds' binding to sites 1 and 2 is cooperative so that the compounds' sensitivity toward synergism for the binding to the cAMP receptor protein in intact cells can be measured.

If the compounds administered together demonstrate synergistic activity in inhibiting the growth of cancer cells, lower total concentrations of both compounds can be used to achieve the same cellular response obtained by otherwise using a single compound.

Cell Culture

All breast cancer cell lines were grown in IMEM supplemented with 10% fetal bovine serum, HEPES 20 mM, penicillin-streptomycin, and extra glutamine. Colon carcinoma cell lines were grown in EMEM supplemented with 10% FBS, EMEM, NEAA, HEPES 20 mM, extra glutamine, and penicillin-streptomycin. The cells were grown at 37° C. in humidified incubators in an atmosphere of 5% $CO_2$.

For cell growth experiments, $2-3 \times 10^5$ cells/60 mm dish were seeded, and 24 hours later (Day 0), the medium was removed, and fresh medium and the additives were added then and every 48 hours thereafter. The compounds of the present invention were added using 100X concentrated stock solutions. At desired times, cell counts in duplicate were performed on a Coulter counter after harvesting the cells with gentle trypsinization.

Preparation of Cell Extracts

All procedures were performed at 0°–4° C. The cell pellets, consisting of $2 \times 10^7$ cells, after two washes with phosphate buffered saline (PBS), were suspended in 0.5 ml buffer 10 (0.1M NaCl, 5 mM $MgCl_2$, 1% Nonidet P-40, 0.5% Na deoxycholate, 2 KIU/ml bovine aprotinin, and 20 mM Tris-HCl, pH 7.4) and homogenized with a Dounce homogenizer for 100 strokes. The homogenates were centrifuged at 700 × g for 20 minutes. The supernatants were used as cell extracts.

DEAE-Cellulose Chromatography of Protein Kinase

The cAMP dependent protein kinase holoenzymes and the regulatory subunits were separated using DEAE-cellulose according to the method of Robinson-Steiner and Corbin, *J. Biol. Chem.* 258: 1032–1040, 1983. The cell pellets, of $2-4 \times 10^7$ cells, after two washes with PBS, were hand homogenized in 3 ml of buffer B (10 mM potassium phosphate containing 1 mM EDTA at pH 6.8) with a Dounce homogenizer, 60 strokes. The homogenates were centrifuged for 20 minutes at 10,000 ×g. The resulting supernatants (2–2.5 ml) were loaded on a 0.9×5.0 cm column preequilibrated with buffer B. After washing, the column was eluted using 60 ml total volume gradient from 0 to 0.4 M NaCl in buffer B with 1.0–1.2 ml fraction volume.

Photoaffinity Labelling of cAMP Receptor Proteins

The photoactivated incorporation of 8-$N_3$[$^{32}$P]cAMP was performed as described by Pomerantz et al., *Biochemistry* 14: 3858–3862, 1975, with a minor modification. The reaction mixtures, final volume of 50 microliters, contained $10^{-6}$M 8-$N_3$[$^{32}$P]±1000-fold excess unlabelled cAMP and samples of 25–50 micrograms protein in buffer 10. The incubations were carried out at 23° C. for 60 minutes in 96-well immunoplates. The reaction mixtures were then irradiated for 30 seconds at 254 nm, placing a Mineralite UVS-11 hand lamp directly onto the plate. The samples were mixed with 25 microliters of 3× sample buffer (3% SDS, 15% beta-mercaptoethanol, 30 mM Tris, 30% glycerol, 1% bromophenol blue saturated solution), boiled for 3 minutes, and centrifuged at 700 × g for five minutes. The samples containing 10–30 micrograms of protein were subjected to 0.05% SDS-12% PAGE. The gels were fixed, dried, and exposed to X-ray films overnight. The protein concentrations were determined by the method of Lowry et al., *J. Biol. Chem.* 193: 265–275, 1951, with bovine serum albumin as standard.

Western Blotting of p21 Protein

Cellular proteins present in cell extracts were separated by 12% SDS-PAGE and transferred to nitrocellulose sheets in transfer buffer (25 mM Tris, 192 mM glycine, 20% methanol, pH 7.4). Nitrocellulose sheets were washed and first incubated with 3% bovine serum albumin in NTE-NP40 (50 mM Tris-HCl, pH 7.5, 150 mM NaCl, 2 mM EDTA, 0.1% Nonidet P-40) for three hours at 37° C. and then sequentially incubated with medium containing p21 monoclonal antiserum Y13–259 directed against the Ha-MuSV-encoded p21 for sixteen hours at 4° C., rabbit anti-rat IgG for 2.5 hours in an ice water bath, and $5 \times 10^5$ cpm/ml $^{125}$I-protein A for one hour in an ice water bath. The nitrocellulose sheets were air dried and exposed to Kodak XAR film for 12–36 hours at −20° C. Comparison of the resulting autoradiograms with others in which normal rat serum was substituted for p21 monoclonal antibody permitted identification of p21. To provide a reference p21, cell lysates were prepared from NIH 3T3 clone 13–3B-4 that had been transfected with HaMuSV DNA.

High-Performance Liquid Chromatography

The cells were washed twice with PBS (centrifuged each time at 700 × g for five minutes), and the pellets were suspended in 0.4 N perchloric acid ($2\times10^7$ cells/ml), vortexed, and centrifuged as above. The supernatants were used in HPLC (100 microliter injections) after filtering through HPLC nylon filters (3 mm/0.45 micrometer pore size).

HPLC was performed using Varian 5500 chromatograph equipped with a Rheodyne model 7125 sample injector, a strong anion exchanger column 12.5 cm, and an LKB 2140 rapid spectral diode array. The nucleotides were eluted with a linear gradient from 0.01M $KH_2PO_4$ (pH 3.83) to 0.8 M $KH_2PO_4$ (pH 3.5). The solvent flow rate was 1.0 ml/min. The column effluent was monitored by the spectra detector between 190 and 370 nm (with 1 nm and 1-s intervals) for 60 minutes. Retention times, peak areas, and absorption spectra were determined by a laboratory computer using LKB 2140-260 COMPARE software.

Cell Cycle Analysis

DNA histograms were generated on FACS II by using the DNA intercalating dye propidium iodide as described by Braylan et al. in *Cytometry* 2: 337–343, 1982. The percentage of cells in each cycle phase was calculated by using a PDP-11/34 computer and software as described by Neckers et al., *Mol. Cell. Biol.* 6: 4244–4250, 1986.

Effect of Site-Selective cAMP Analogues on Growth Inhibition

A variety of cAMP analogues, modified at either the C-6 or C-8 position or both the C-6 and C-8 positions of the adenine moiety, were tested for their growth inhibitory effect on cancer cell lines. The studies reported in Table 1 were carried out by measuring cell growth by counting the cell number at Day 3 and Day 4 after treatment of the cells with each individual compound at several concentrations on Day 0 and Day 2. Cell counts were performed on each of three or more separate experiments, and the average values are expressed as percent growth inhibition as compared with untreated control cells.

TABLE 1

Effect of site-selective cAMP analogues on the growth of breast (MCF-7) and colon (LS-174T) cancer cell lines cAMP Analogues are listed in order from the most to the least potent for a given modification on the adenine ring.

| | | % Growth Inhibition[a] | |
|---|---|---|---|
| | Cyclic nucleotide analogue added (50 μM) | | |
| | | Day 3 | Day 4 |
| C-8 | 8-Chloro | 67(62–75) | 75(68–81) |
| | 8-Methylthio | 46(42–52) | 42(38–50) |
| | 8-Bromo | 41(37–44) | 40(35–45) |
| | 8-Iodo | 26(20–31) | 25(23–27) |
| | 8-p-chlorophenylthio | 23(19–27) | 24(20–26) |
| | 8-β-hydroxyethylamino | 15(12–17) | 20 (15–23) |
| | 8-Methylamino | 14(10–16) | 15(12–18) |
| | 8-N,N-Dimethylamino | 0(0) | 0(0) |
| C-6 | $N^6$-Benzyl | 56(49–60) | 70(65–74) |
| | $N^6$-Ethoxycarbonyl | 32(27–40) | 40(36–43) |
| | $N^6$-Benzoyl | 30(26–38) | 28(25–32) |
| | $N^6$-Phenylcarbamoyl | 10(8–12) | 10(5–12) |
| | $N^6$-Butyryl | 0(0) | 0(0) |
| | $N^6$-$O^2$-Dibutyryl | 0(0) | 0(0) |
| C-6,-8 | $N^6$-Phenyl-8-p-chlorophenylthio | 60(56–63) | 47(44–55) |

TABLE 1-continued

Effect of site-selective cAMP analogues on the growth of breast (MCF-7) and colon (LS-174T) cancer cell lines cAMP Analogues are listed in order from the most to the least potent for a given modification on the adenine ring.

| | % Growth Inhibition[a] | |
|---|---|---|
| Cyclic nucleotide analogue added (50 μM) | | |
| | Day 3 | Day 4 |
| $N^6,N^6$-Diethyl-8-p-chlorophenylthio | 43(40–50) | 45(40–49) |
| 6-Piperidino-8-p-chlorophenylthio | 33(30–37) | 25(21–30) |
| $N^6$-Benzyl-8-benzylthio | 25(20–30) | 23(20–25) |
| $N^6$-n-Butyl-8-p-chlorophenylthio | 15(12–17) | 22(20–24) |

[a]The values of percentage growth inhibition were determined from the dose-response curve experiments. Each value represents an average value and range (in parentheses) obtained from three or more separate experiments. The cell counts in duplicate were performed at day 3 and day 4 after two treatments (day 0 and day 2) with analogs (seeding on day −1).

Table 1 above shows the growth inhibitory effect of 19 site-selective compounds on the breast (MCF-7) and colon (LS-174T) cancer cell lines. The compounds are listed in order from the most to the least potent for growth inhibition for a given modification on the adenine ring. As shown in Table 1, analogues modified with a halogen or thio moiety at the C-8 position were more potent than those modified with an amino moiety at the C-8 position. Thus, at 50 micromolar concentration, 8-Cl-, 8-methylthio-, and 8-bromo-cAMP exhibited 40–75% growth inhibition, while 8-β-hydroxylamino-, 8-methylamino-, and 8-N,N-dimethylamino-cAMP exhibited growth inhibition of only ≦20%. C-6 analogues were generally less potent in growth inhibition than the C-8 analogues and C-6, C-8 analogs even less potent. At 50 micromolar concentration, $N^6$-benzyl-, and $N^6$-ethoxycarbonyl-cAMP demonstrated 30–70% growth inhibition. DibutyrylcAMP, an earlier known analogue, at 50 micromolar concentration, exhibited no growth inhibition. The C-6,-8-analogue, $N^6$-phenyl-8-p-chlorophenylthio-cAMP, which is structurally similar to both $N^6$-benzyl- and 8-Cl-cAMP, exhibited the most potent growth inhibition among the C-6,-8 disubstituted analogues.

Figure 1:
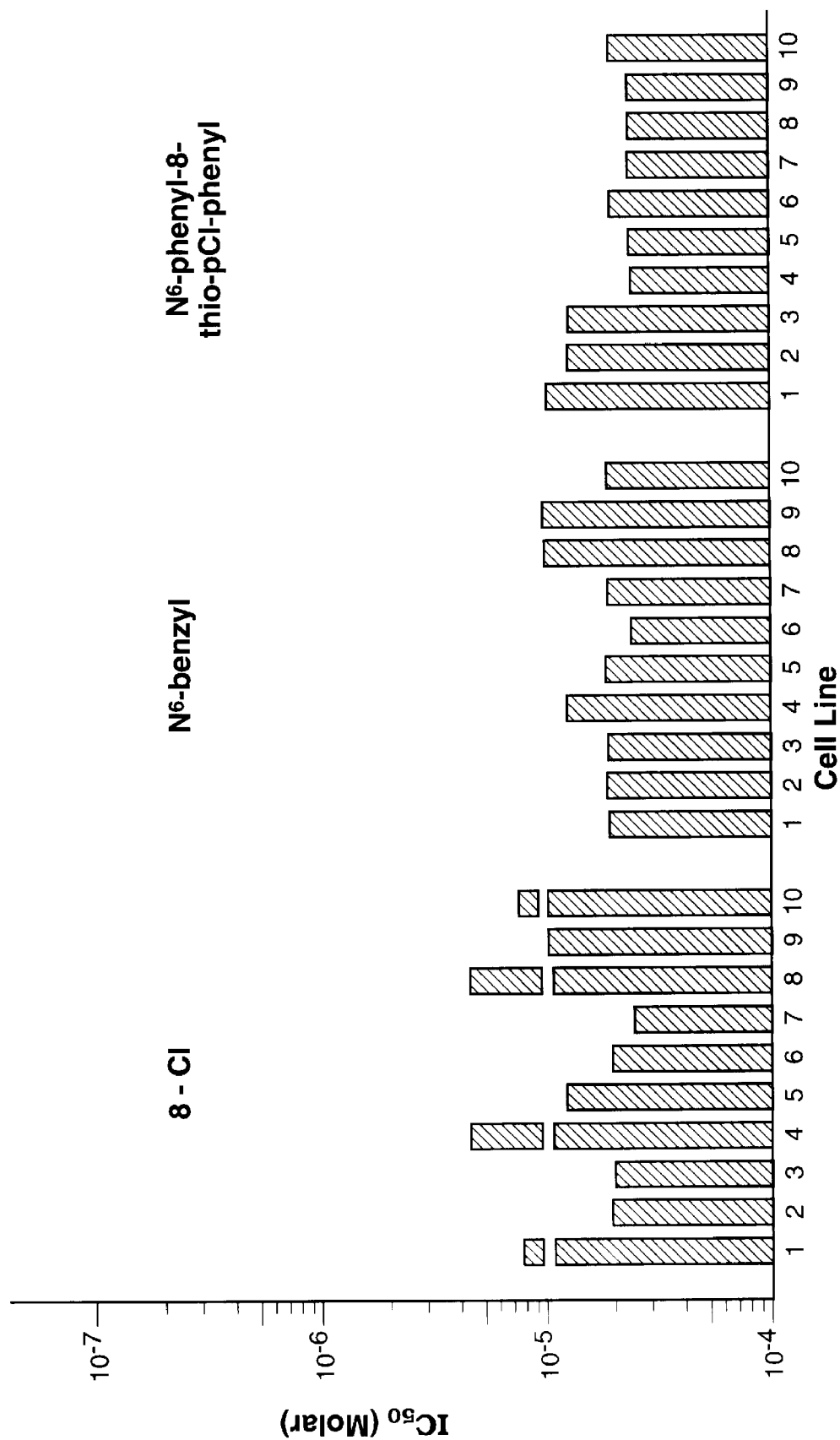
FIG. 1 shows the growth inhibition of breast and colon cancer lines by site-selective cAMP analogues.
Figures 2A, 2B:
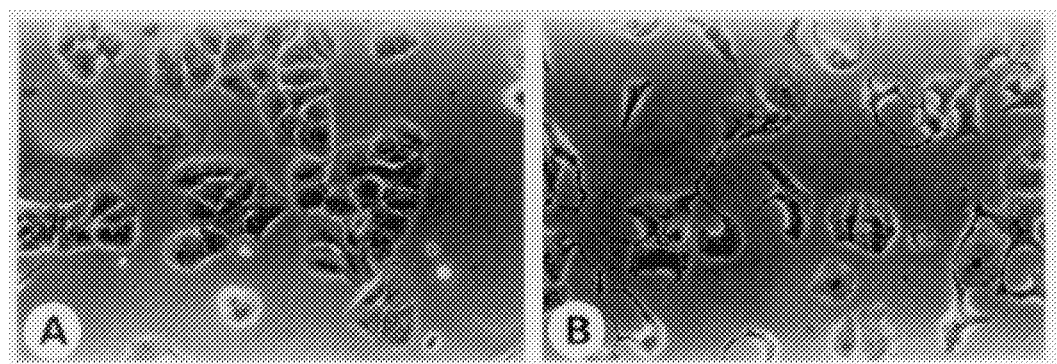
Figures 2C, 2D:
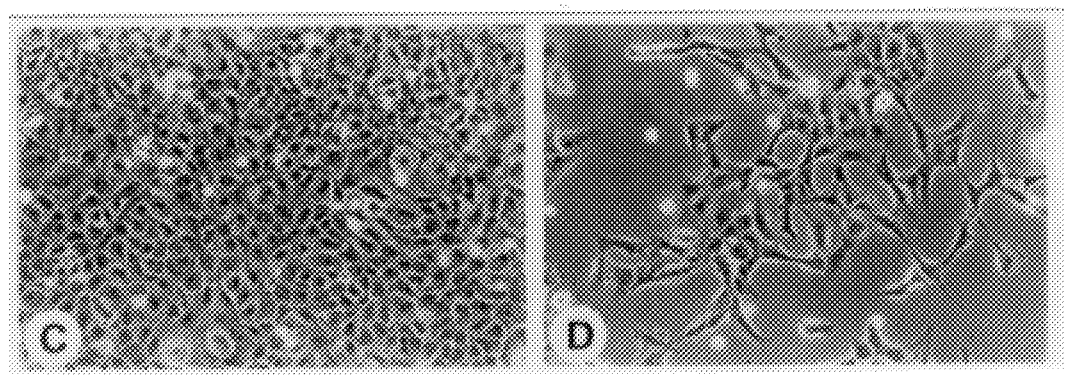
Figures 2E, 2F:
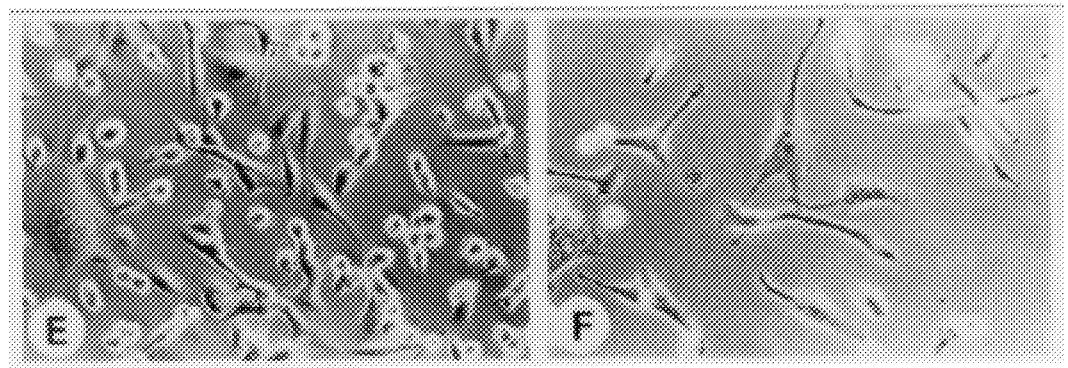
Figures 2G, 2H:
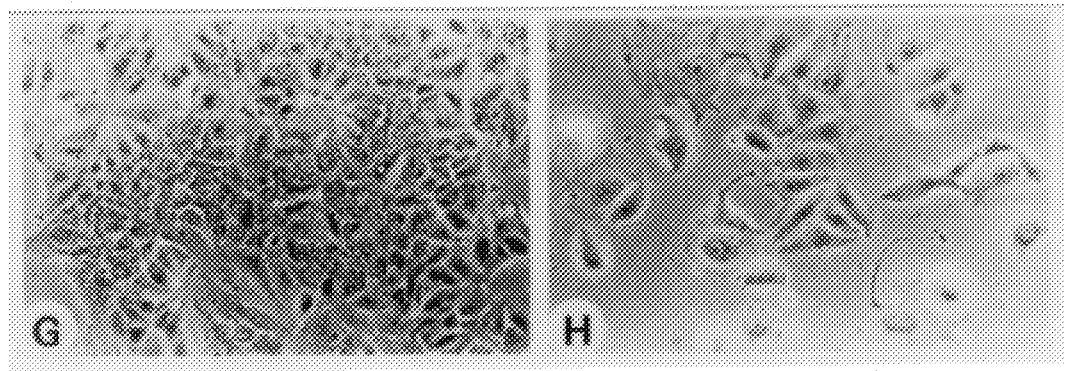

FIG. 1 shows the growth inhibitory effect of the three most potent compounds, 8-Cl, $N^6$-benzyl-, and $N^6$-phenyl-8-p-chlorophenylthio-cAMP, on the breast and colon cancer lines. These analogues demonstrated 50% growth inhibition at $5-25\times10^{-6}$ to $2.5\times10^{-5}$M concentrations ($IC_{50}$) in all ten cancer lines tested. Thus, the site-selective compounds exhibited potent growth inhibition in the hormone-dependent (MCF-7, T-47D, ZR-75-1) and hormone-independent (MDA-MB-231, MCF-7ras, BT-20) breast cancer lines as well as colon cancer lines at micromolar concentrations. As previously reported by Cho-Chung, *Cell. Mol. Biol.* 26: 395–403, 1980; Cho-Chung et al., *Science* 214: 77–79, 1981; and Fentiman et al., *Mol. Biol. Med.* 2: 81–88, 1984; dibutyrylcAMP or $N^6$-butyrylcAMP at millimolar concentrations showed growth inhibition only in the hormone-dependent breast cancer lines but not in the hormone-independent breast and colon cancer cell lines. Phosphodiesterase inhibitors, such as theophylline (0.1 mM) or 1-methyl-3-isobutylxanthine (0.5 mM), each alone had little or no growth inhibitory effect, particularly on the hormone-independent breast and colon cancer lines, and these inhibitors could not enhance the effect of the site-selective compounds even when added in combination with the site-selective compounds. The effect of the site-selective cAMP analogues on growth inhibition appears to be more selective toward transformed cancer cells than nontransformed cells, since the site-selective compounds were 50–70% less potent for nontransformed NIH/3T3 cells compared with the Ha-MuSV-transformed NIH/3T3 clone 13-3B-4 cells.

Effect of Combinations of Compounds on Growth Inhibition

Previous in vitro studies have demonstrated that binding of a cAMP analogue selective for either intrachain site on the regulatory subunit of protein kinase stimulates binding of a cAMP analogue selective for the other site, Rannels et al., *J Biol. Chem.* 256: 7871–7876, 1981; Corbin et al., *Eur. J. Biochem.* 125: 259–266, 1982, and two such site-selective compounds in combination demonstrate synergism on protein kinase activation, Robinson-Steiner et al., *J. Biol. Chem.* 258:1032–1040, 1983, and Ogreid et al., *Eur. J. Biochem.* 150:219–227, 1985. Synergism of two classes of site-selective cAMP analogues has been demonstrated in lipolysis in isolated adipocytes by Beebe et al., *J. Biol. Chem.* 259: 3539–3547, 1984, and in growth inhibition of HaMuSV-transformed NIH 3T3 cells, Tagliaferri et al., *Biochem. Biophys. Res. Commun.* 130:1193–1200, 1985.

To test the effect of cAMP analogue combinations, C-8 analogues, which are site 1-selective, and C-6 analogues, which are site 2-selective, were combined such that alone they exhibit growth inhibition of 10–20% each, and the effects were quantified by synergism quotient. Synergism quotient was defined as the net growth inhibitory effect of the analogue combination divided by the sum of the net analogue effects on growth inhibition. A quotient of >1 indicates a synergistic effect, while a quotient of <1 indicates an antagonistic effect. Considering especially that the C-6, -8 compounds are less potent than either the C-6 or C-8 compounds, it is most surprising that the combined use of C-6 and C-8 compounds is even better than the use of either C-6 or C-8 compounds alone.

Table 2 shows representative examples of synergism between C-6 and C-8 analogues in growth inhibition of the MCF-7ras cell line. 8-Cl-cAMP (1 μM) in combination with either $N^6$-benzyl- or $N^6$-benzoyl-cAMP produced the greatest degree of growth inhibition compared with that expected from the sum of the individual analogues alone, having a synergism quotient of 1.71 to 1.83. 8-Cl-cAMP in combination with either $N^6$-benzyl- or $N^6$-benzoyl-cAMP (0.5 μM), therefore, produced the growth inhibitory effect that is almost equivalent to that shown by 20-20 μM concentrations of either 8-Cl-cAMP or the $N^6$-analogues alone. The $N^6$-analogues also demonstrated synergism of growth inhibition with other C-8 analogues, such as 8-methylthio-cAMP (synergism quotient 1.50–1.84) and 8-bromo-cAMP (synergism quotient 1.5). Only a limited degree of synergism was noted, however, when the $N^6$-analogues were combined with 8-amino derivatives (synergism quotient 1.12–1.25). Thus, the $N^6$-analogues acted far more synergistically when in combination with 8-thio or 8-halogen derivatives than with 8-amino derivatives. Similar synergism of growth inhibition by the C-6 and C-8 analogue combination was also demonstrated in other breast and colon cancer cell lines. Synergism of growth inhibition was only seen when a site 1-selective analogue was added with a site 2-selective analogue, but not when two site 1-selective or two site 2-selective analogues were combined. Two such examples are shown in Table 2.

TABLE 2

Synergistic growth inhibitory effect of C-6 and C-8 analogue combination in MCF-7ras breast cancer cell line Synergism of growth inhibition was determined by treatment of cells with C-6 analogues and C-8 analogues alone and in combination at Day 0 and Day 2 and counting the cell number at Day 4.

| Analogue combination | μM | % Growth inhibition[a] | Synergism quotient[b] |
|---|---|---|---|
| 8-Chloro | 1.0 | 60(57–62) | 1.71 |
| + | | | |
| $N^6$-Benzyl | 0.5 | | |
| 8-Chloro | 1.0 | 55(47–57) | 1.83 |
| + | | | |
| $N^6$-Benzoyl | 0.5 | | |
| 8-Methylthio | 1.0 | 45(40–52) | 1.50 |
| + | | | |
| $N^6$-Benzyl | 0.5 | | |
| 8-Methylthio | 1.0 | 46(40–55) | 1.84 |
| + | | | |
| $N^6$-Benzoyl | 0.5 | | |
| 8-Methylamino | 1.0 | 28(20–30) | 1.12 |
| + | | | |
| $N^6$-Benzyl | 0.5 | | |
| 8-Methylamino | 1.0 | 25(20–27) | 1.25 |
| + | | | |
| $N^6$-Benzoyl | 0.5 | | |
| 8-Chloro | 1.0 | 30(22–32) | 0.86 |
| + | | | |
| 8-Methylthio | 1.0 | | |
| $N^6$-Benzyl | 0.5 | 20(18–25) | 0.80 |
| + | | | |
| $N^6$-Benzoyl | 0.5 | | |

[a]Data are expressed as percentage growth inhibition in reference to the growth of untreated control cells and represent average values and ranges (in parentheses) of duplicate cell counts on three or more separate experiments. The values for percentage growth inhibition of each analogue when added alone were 20% (8-Cl-cAMP), 15% (methylthio-cAMP), 10% (8-methylamino-cAMP), 15% ($N^6$-benzyl-cAMP), and 10% ($N^6$-benzoyl-cAMP).
[b]The synergism quotient was defined as previously described.

Effect of cAMP Analogues on Cell Morphology

The growth inhibitory effect of the site-selective cAMP analogue correlated with a change in the cell morphology. As shown in FIG. 2, both hormone-dependent (A) and -independent breast (C,E, and G) cancer cells demonstrated a characteristic morphological change after treatment with 50 μM 8-Cl-cAMP for four to five days. The cells exhibited an enlargement of cytoplasm with stretched fibroblast-like appearance (B,D,F, and H). Treatment of breast and colon cancer cells with $N^6$-benzyl-cAMP (50 μM), and 8-methylthio-cAMP (100 μM) for three to four days all induced the morphological change. Furthermore, the synergistic growth inhibitory effect of C-6 and C-8 analogue combinations was also reflected in the change in the cell morphology. Thus, treatment of cells with either 1 μM 8-Cl-cAMP or 0.5 μM $N^6$-benzyl-cAMP for four days did not induce a change in the cell morphology, whereas when the cells were treated in combination with 8-Cl-cAMP (1 μM) and $N^6$-benzyl-cAMP (0.5 μM), the cells exhibited the morphological change. The same synergism was demonstrated between the other $N^6$-analogues and C-8 analogues that demonstrated the synergism of growth inhibition.

Effect of 8-Cl-cAMP and 8-Cl-Adenosine on Growth and Cell Cycle Progression

The growth inhibitory effect of the site-selective cAMP analogues were examined to determine if there was also a cytotoxic effect due to an adenosine metabolite. FIG. 3 shows time courses of 8-Cl-cAMP and 8-Cl-adenosine in their growth inhibition and release from the inhibition in the LS-174T colon cancer line. While the untreated control cells showed a logarithmic increase in cell number, cells treated with either 8-Cl-cAMP or 8-Cl-adenosine exhibited a marked reduction in cell growth and eventually stopped replicating within three to four days. Upon cessation of treatment, the cells treated with either 8-Cl-cAMP for up to nine days resumed growth almost immediately, and the rate of cell growth became similar to that of untreated control cells within a few days, whereas the 8-Cl-adenosine-treated cells remained growth inhibited and did not resume their growth up to two weeks after the release from the treatment. Thus, the growth inhibition produced by 8-Cl-cAMP and 8-Cl-adenosine was mediated through two different mechanisms; the former by a decrease in the rate of replication without affecting cell viability, and the latter by cell killing.

A determination was made whether the reduced cell proliferation observed in the cancer cell lines after treatment with the compounds of the present invention is due to a specific block in one phase of the cell cycle. As shown in Table 3, the fractions of cells in $G_1$, S, and $G_2$/M phases were not appreciably different between the control cells (untreated) and the cells treated with either 8-Cl-cAMP or $N^6$-benzyl-cAMP. Thus, the inhibition of cell growth induced by the cAMP analogues was not associated with a specific block in one phase of the cell cycle. However, 8-Cl-adenosine treatment induced an appreciable increase of the cell population in $G_1$ phase with a marked reduction in S-phase.

TABLE 3

Effect of site-selective cAMP analogues and 8-Cl-adenosine on cell cycle progression of breast and colon cancer cell lines
Breast (MCF-7, MDA-MB-231) and colon (LS-174T) cancer cells in log phase (untreated control) and 3 days after treatment with 8-C1-cAMP (10 µM), $N^6$-benzyl-cAMP (35 µM), and 8-Cl-adenosine (5 µM) were analyzed for DNA content by flow cytometric analysis as described below. Similar results were obtained with other breast and colon cancer cell lines.

| | | % Cell Population in: | | | |
|---|---|---|---|---|---|
| Cell line | Treatment | $G_1$ | S | $G_2$M | % Growth |
| MCF-7 | Control | 52 | 23 | 25 | 100 |
| | 8-Cl (10 µM) | 53 | 22 | 25 | 40 |
| MDA-MB-231 | Control | 57 | 25 | 18 | 100 |
| | N6-benzyl (35 µM) | 60 | 25 | 15 | 45 |
| LS-174T | Control | 60,52[a] | 17,23 | 23,25 | 100,100 |
| | 8-Cl (10 µM) | 63,53 | 15,22 | 22,25 | 30,32 |
| | 8-Cl-adenosine (5 µM) | 72,68 | 8,14 | 20,18 | 30,30 |

[a]The paired numbers were derived from two separate experiments.

HPLC Analysis of Cell Extracts After Treatment of Cancer Cells with cAMP Analogues An shown in FIG. 4, the cell extracts from HT-29 colon cancer cell line treated for 72 hours with 50 µM of 8-Cl-cAMP demonstrated several distinct peaks that are not present in the untreated control cell extracts. In reference to the elution profiles of the standard nucleotides, these peaks were identified to be 8-Cl-cAMP (peak a), 8-Cl-AMP (peak b), 8-Cl-ADP (peak c), and 8-Cl-ATP (peak f). The peak at approximately 1.5 minutes retention time was identical in both treated and untreated cell extracts. This peak would contain adenosine and 8-Cl-adenosine if they were present in the sample. In fact, no 8-Cl-adenosine was present in this peak as verified by absorption spectra. In the medium from the cells treated for 49 hours with 8-Cl-cAMP (50 µM), a single large peak of 8-Cl-cAMP was detected, but no 8-Cl-adenosine was present. These data showed that the intact 8-Cl-cAMP, without being metabolized by the membrane-bound phosphodiesterase, penetrated the cell, and a portion of 8-Cl-cAMP was converted to 8-Cl-AMP, 8-Cl-ADP and 8-Cl-ATP. Treatment of cells with 8-Cl-AMP at concentrations as high as 100 µM, however, produced no appreciable growth inhibition.

The Effect of cAMP Analogues on the Levels of RI and RII cAMP Receptor Proteins

Figure 5A:
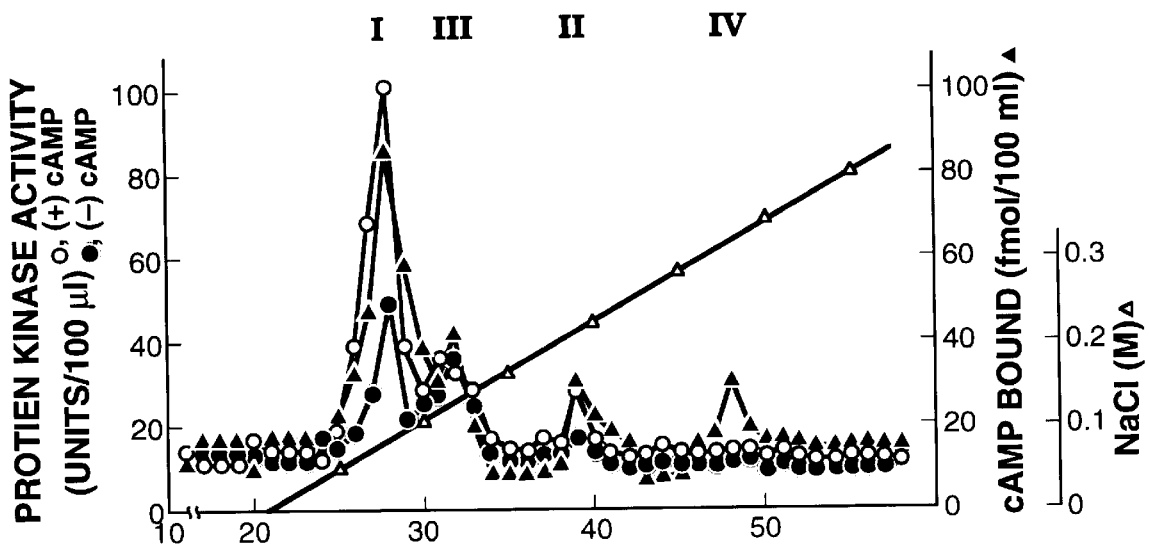

The synergistic effect demonstrated on the growth inhibition of the cancer cells by the C-6 and C-8 thio or C-8-halogen derivatives of cAMP analogues in combination indicated a response of type II protein kinase rather than type I kinase in the analogue effect. The relative proportions of free RI and RII and holoprotein kinases, type I and type II, were determined using DEAE-cellulose chromatography. Chromatography of the cytosols from treated and untreated LS-174T cells is shown in FIG. 5. The catalytic subunit was eluted before the start of the NaCl gradient. The untreated cells, FIG. 5A, showed two major peaks, peaks 1 and 2, of cAMP-dependent protein kinase activity that were coincident with peaks of cAMP binding activity. Peak 1 eluted at 0.07M NaCl, and peak 2 eluted at 0.22M NaCl, and the kinase and binding activities of peak 1 were approximately three-fold that of peak 2. In addition, two minor cAMP binding peaks, peaks 3 and 4, with no cAMP-dependent protein kinase activity eluted at 0.13M NaCl and 0.30M NaCl, respectively. Autoradiography after photoaffinity labelling of the fractions of the eluents with 8-azido-[$^{32}$P]-cAMP and performing SDS-PAGE showed that peaks 1 and 3 contained the 48,000 Mr RI, whereas peaks 2 and 4 contained the 52,000 Mr RII. These results suggest that peaks 1 and 2 are similar to types I and II holoprotein kinases, and peaks 3 and 4 are similar to free RI and RII subunits found in mammalian tissue cytosols.

Figure 5B:
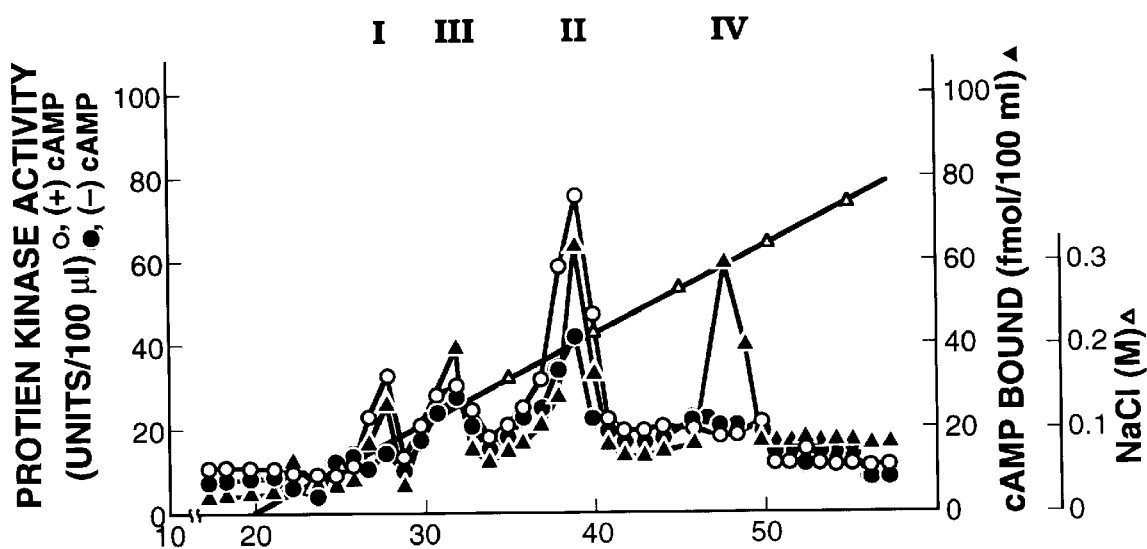

When the cells were treated for three days with $N^6$-benzyl-cAMP (0.5 µM) plus 1 µM of 8-Cl-cAMP, the chromatographic pattern was considerably altered, as shown in FIG. 5B. Both cAMP-dependent protein kinase activity and cAMP binding activity of peak 1 decreased to 30% of those in the untreated cells, while the cAMP-stimulated kinase and cAMP binding activities of peak 2 increased three-fold and two-fold, respectively. In addition, peak 4 cAMP binding activity increased two-fold over that of untreated control cells, while peak 3 remained without appreciable change. Thus, decrease of type I holoenzyme, peak 1, was accompanied by an increase of both type II holoenzyme, peak 2, and RII subunit, peak 4. A similar change in the elution profile was observed when the cells were treated with other combinations of C-6 and C-8 analogues that showed synergism in growth inhibition, whereas each of these compounds alone, at 1 µM concentration, exhibiting little or no growth inhibition, caused no apparent change in the elution profile. Thus, the same synergism of C-6 and C-8 analogue combinations was observed in protein kinase change as that observed for growth inhibition. When intact untreated cells were washed just before collection with the analogue combination-containing medium, the elution profile was the same as that of cytosol from untreated cells. Thus, the change in peaks 1, 2, and 4 observed in the analogue-treated cells was not a consequence of residual analogue from the medium interacting with the cytosol during cell homogenization.

The increase in peaks 2 and 4 observed after the analogue treatment suggests that the analogue caused both dissociation and increase of type II protein kinase. Furthermore, the presence in the treated cells of a considerable amount of type II holoenzyme, peak 2, suggests that peak 2, at least in part, may contain a partially dissociated form of holoenzyme, such as $R_2C$, which may not be resolved from $R_2C_2$ by DEAE-cellulose chromatography.

Since the type I and type II protein kinases differ only in their regulatory subunits, i.e., the cAMP binding receptor protein, while the catalytic subunits are identical, the receptor protein was measured during treatment of the cancer cells.

As shown in FIG. 6, the untreated breast (MDA-MB-231) and colon (LS-174T) cancer cells contained a major cAMP receptor protein with a Mr of 48,000, lane 4. This protein appears to be the RI cAMP receptor protein, i.e., the regulatory subunit of type I kinase, because it comigrated in SDS-PAGE with the purified preparation of the 48,000 Mr RI (lane RI) from rabbit skeletal muscle. When the cells were treated for three days with 8-Cl- cAMP, lane 1, or $N^6$-benzyl-cAMP (lane 2), the cAMP receptor protein with a molecular weight of 52,000 increased appreciably with concomitant decrease of the 48,000 RI receptor protein. The 52,000 Mr protein appears to be the RII cAMP receptor protein because the Mr 50,000–52,000 cAMP receptor proteins have been identified as the RII receptor protein in various tissues. When the cells were treated with DBcAMP, which did not inhibit cell growth, the RI and RII receptor levels remained unchanged, as can be seen by comparing lane 3 with lane 4.

Quantification by densitometric tracings of the autoradiograms showed that the cancer lines treated with 8-Cl-cAMP or $N^6$-benzyl-cAMP, exhibiting 45–70% growth inhibition, demonstrated a 70–80% decrease in the RI level and a two- to three-fold increase in the ratio of RII to RI. DBcAMP in a concentration of 1 mM, a weak growth inhibitor (15%), did not appreciably affect the RI or RII receptor levels, as shown in the Table 10.

Effect of cAMP Analogues on the p21 ras Protein Level

The site-selective cAMP analogues of the present invention have been found to bring about a reduction in the level of a cellular transforming gene product, p21 ras protein, in parallel to their growth inhibitory effect. As shown in FIG. 7, Western blotting analysis of p21 protein demonstrated that the MCF-7 cells treated with 10 $\mu$M 8-Cl-cAMP for three days, exhibiting 57% growth inhibition (cf. Table 11), contained a markedly decreased level of p21, as shown in FIG. 7, lane 2. A similar decrease in p21 protein was observed in the cells treated with $N^6$-benzyl-cAMP. A weaker growth inhibitor, DBcAMP (500 $\mu$M), which produced only 20% growth inhibition, as shown in Table 11, caused a slight reduction in p21 level, lane 4. 8-Cl-adenosine, 5 $\mu$M, though exhibiting strong growth inhibition, did not appreciably affect the p21 level, as shown in lane 3 of FIG. 7. Thus, 8-Cl-adenosine, producing growth inhibition through a different mechanism from that of 8-Cl-cAMP, failed to produce a biochemical change inducible with the cAMP analogues.

Effect of 8-Cl-cAMP on In Vivo Tumor Growth

The antitumor activity of 8-Cl-cAMP has been evaluated in a number of in vivo experimental tumor models. Initial data obtained with the intraperitoneally inoculated L1210 leukemia and intraperitoneal treatment suggested that a sustained presence of the cAMP derivative was required for antitumor activity. The maximum non-lethal dosage of the compound in non-tumored $BDF_1$ mice was 104 mg/kg. This dosage, when given as a bolus injection for seven consecutive days, was tolerated by L1210-bearing mice but demonstrated no antitumor effect. However, constant infusion of the cyclic nucleotide at a dosage of 104 mg/kg/day for five days caused a 37% increase in mean life span.

Based on the findings with the L1201 leukemia model, the efficacy of the 8-Cl-cAMP-Na+infusions were evaluated in advanced-stage human tumor xenograft models. Tumor fragments of approximately 14 mg were implanted subcutaneously in athymic CD-1 female mice and seven day intraperitoneal infusions of the cyclic nucleotide were initiated three weeks later when mean tumor weights had reached 300–400 mg. Tumor measurements were recorded on the initial day of treatment (staging day) and one day after treatment was completed (staging day +7), and were used to calculate changes in tumor weights. The data obtained with two mammary, one lung, and one colon tumor (cf. Tables 8 and 9) indicated that infusions of 8-Cl-cAMP-Na+ caused tumor stasis during treatment. In another study, a subcutaneous infusion of approximately 42 mg/kg/day (1 mg/mouse) for seven days appeared to be toxic to athymic NCR-NU mice bearing advance-stage human LoVo colon tumors of about 300 mg. An infusion of 0.67 mg/mouse/day caused only a minor tumor growth delay. In short-term assays (seven days) using the transplantable DMBA-1 and MNA-2 rat mammary carcinomas, it was found that pellets of 8-Cl-cAMP implanted at the time of tumor transplantation caused 40–50% inhibition of tumor growth.

As shown in Table 4, the 8-Cl-cAMP 10 mg pellet implanted twice every two weeks completely stopped tumor growth. Treated tumors regress almost 100% within 30 days. DBcAMP treatment only arrests this tumor growth without producing regression.

TABLE 4

Effect of 8-Cl-cAMP pellet on the in vivo growth of DMBA-induced mammary carcinomas in rats

| Treatment | Total tumor no. | Mean tumor measurement (cm) | | Mean % of change in tumor volume |
|---|---|---|---|---|
| | | Day 0 | Day 30 | |
| None | 20 | 1.2 × 1.5 | 2.2 × 3.2 | +760 ± 150[a] |
| 8-Cl pellet[b] | 20 | 1.3 × 1.8 | 0.3 × 0.5 | −96 ± 20 |

[a]Mean ± S.E.
[b]8-Cl-cAMP (20 mg pellet per rat, consisting of 10 mg 8-Cl-cAMP and 10 mg cholesterol), was implanted on day 0 and day 14.

As shown in Table 5, these tumors are completely resistant to DB-cAMP. The 8-Cl-cAMP 10-mg pellet caused 40–50% growth inhibition within one week. A continuous supply of 8-Cl-cAMP with an osmotic pump may produce greater inhibitory effect. Alternatively, the compound may be administered in time-release form or in time-release liposomes.

As shown in FIG. 8, 8-Cl-cAMP (10 mg pellet) implantation one day before the carcinogen DMBA intubation resulted in 30 days of delay in the first tumor appearance and 70% reduction in the total number of tumors produced as compared with the effect of DMBA only. The results indicate the effect of 8-Cl-cAMP on blocking of the initiation stage of DMBA carcinogenesis.

The following data show the effect of 8-Cl-cAMP on the growth of malignant neoplasms in vivo:

TABLE 5

Effect of 8-Cl-cAMP pellet in the in vivo growth of transplantable, hormone-independent, and metastatic rat mammary carcinomas (DMBA-1, NMU-2) and LS-174T human colon carcinoma line

| Host | Tumor | Treatment | Total tumor no. | Change in mean tumor volume (cm$^3$) | (%) |
|---|---|---|---|---|---|
| rat | transpl. | none | 15 | 2.63 | 100 |
|  | DMBA-1 | 8-Cl | 15 | 1.60 | 61 |
|  |  | DB | 15 | 2.60 | 9 |
|  | metastatic | none | 15 | 2.14 | 100 |
|  | NMU-2 | 8-Cl | 15 | 1.10 | 51 |
|  |  | DB | 15 | 2.15 | 100 |
| nude | LS-174T | none | 10 | 0.97 | 100 |
| mouse |  | 8-Cl | 10 | 0.58 | 60 |

DMBA-1, a variant of primary hormone-dependent DMBA tumor, hormone-independent and transplantable.
NMU-2, a variant of primary hormone-responsive NMU tumor, hormone-independent, transplantable, and metastatic.
LS-174T, human colon cancer line was s.c. grown in nude mice and a solid tumor, transplantable, was obtained.
8-Cl-cAMP and DB-cAMP were given as a 20-mg pellet consisting of 10 mg of cAMP analogue and 10 mg cholesterol on day 0, and change in tumor volume was measured on day 7.

TABLE 6

Influence of 8-Cl-cAMP-Na$^+$ on the life span of non-tumor BDF$_1$ mice when delivered i.p. by bolus injection

| Dosage mg/kg/inj | Route and schedule of delivery | Toxic deaths No. killed/No. treated |
|---|---|---|
| 480 | ip; qd, day 1 | 5/5 |
| 288 | ip; qd, day 1 | 5/5 |
| 173 | ip; qd, day 1 | 2/5 |
| 104 | ip; qd, day 1 | 0 |
| 62 | ip; qd, day 1 | 0 |
| 37 | ip; qd, day 1 | 0 |
| 22 | ip; qd, day 1 | 0 |

When delivered qd, day 1 to non-tumor BDF$_1$ mice, the 480 and 288 mg/kg dosages of 8-Cl-cAMP-Na$^+$ were lethally toxic for all treated mice. The 173 mg/kg dosage killed 2 of 5 mice and lower dosages were not lethally toxic.

TABLE 7

Influence of 8-Cl-cAMP-Na$^+$ on the postinoculation lifespan of L1210-inoculated BDF$_1$ mice when infused or delivered by bolus injection

| Dosage Postinoculation (mg/kg/day) | Route and schedule of delivery | lifespan (T/C) |
|---|---|---|
| 104 | ip; qd, day 1–7 | 98 |
| 62 | ip; qd, day 1–7 | 103 |
| 37 | ip; qd, day 1–7 | 93 |
| 22 | ip; qd, day 1–7 | 103 |
| 800 | ip; 24-hr infusion, day 1–5 | 62 toxic |
| 480 | ip; 24-hr infusion, day 1–5 | 93 toxic |
| 288 | ip; 24-hr infusion, day 1–5 | 128 toxic |
| 173 | ip; 24-hr infusion, day 1–5 | 131 |
| 104 | ip; 24-hr infusion, day 1–5 | 137 |
| 62 | ip; 24-hr infusion, day 1–5 | 137 |
| 37 | ip; 24-hr infusion, day 1–5 | 126 |
| 22 | ip; 24-hr infusion, day 1–5 | 126 |
| 13 | ip; 24-hr infusion, day 1–5 | 113 |
| 4.8 | ip; 24-hr infusion, day 1–5 | 100 |
| 1.7 | ip; 24-hr infusion, day 1–5 | 100 |
| 0.6 | ip; 24-hr infusion, day 1–5 | 100 |

Mice were inoculated i.p. with 1 × 10$^6$ cells of murine leukemia L1210 24-hr before first treatment. Each treatment group consisted of 5 mice. Twenty control mice that received a 0.9% solution of NaCl lived 6.2 ± 0.6 days. When infused, the 800 and 480 mg/kg dosages of 8-Cl-cAMP-Na$^+$ were lethally toxic for all treated mice while the 288 mg/kg dosage killed 2 to 5 mice. Infusions by Harvard pumps.
Single ip dose
LD$_{50}$ - 195 mg/kg
LD$_{10}$ - 122 mg/kg

TABLE 8

Effects of 8-Cl-cAMP-Na$^+$ on the Growth of Human Mammary Tumor Xenografts

| Xenograft | Ip infusion (mg/kg/day) for 7 days) | Initial Mean Tumor Wt (mg)* | Final Mean Tumor Wt (mg)$ | % Δ T/T** or % Δ T/ΔC$$ |
|---|---|---|---|---|
| MX-1 mammary | control | 334 | 549 |  |
| carcinoma | 173 | 375 | 336 | −10 |
|  | 104 | 346 | 323 | −07 |
|  | 62 | 337 | 288 | −15 |
| MDA-MB-231 | control | 361 | 726 |  |
| mammary | 104 | 367 | 433 | +18 |
| carcinoma | 62 | 375 | 471 | +26 |
|  | 37 | 367 | 516 | +41 |

*Mean tumor weight per group on staging day.
$Mean tumor weight per group on staging day +7.
**Change in test tumor wt (final-initial)/initial test tumor treatment. Denoted by negative value.
$$Change in test tumor wt/change in control tumor wt. Used where test tumor size increased during treatment. Denoted by positive value.

TABLE 9

Effects of 8-Cl-cAMP-Na$^+$ on the Growth of Human Colon and Lung Tumor Xenografts

| Xenograft | Ip infusion (mg/kg/day) for 7 days | Initial Mean Tumor Wt (mg)* | Final Mean Tumor Wt (mg)$ | % Δ T/T** or % Δ T/ΔC$$ |
|---|---|---|---|---|
| LOVO Colon | Control | 292 | 376 |  |
| carcinoma | 104 | 288 | 317 | −35 |
|  | 62 | 293 | 290 | −01 |
|  | 37 | 288 | 284 | −01 |
| LX-1-Lung | Control | 332 | 515 |  |
| carcinoma | 104 | 324 | 270 | −17 |
|  | 62 | 327 | 277 | −15 |
|  | 37 | 330 | 341 | +06 |

*Mean tumor weight per group on staging day.
$Mean tumor weight per group on staging day +7.
**Change in test tumor wt (final-initial)/initial test tumor treatment. Denoted by negative value.
$$Change in test tumor wt/change in control tumor wt. Used where test tumor size increased during treatment. Denoted by positive value.

It can be seen from the above that the site-selective analogues of cAMP are effective in arresting tumor growth at micromolar concentrations. The site-selective analogues, which are known to be many fold more active in their binding to the cAMP receptor protein, and, therefore, in cAMP-dependent protein kinase activation than the early known analogues in vitro, demonstrated their effectiveness at many fold lower concentrations. Thus, cAMP-dependent protein kinase may be directly involved in the growth inhibition produced by the site-selective analogues tested here.

Table 10 shows the densitometric tracings of the autoradiograms at $A_{560}$ nm. The levels of the receptor proteins are expressed relative to the RI level in the untreated control cells of MDA-MB-231 and LS-174T which are each set equal to 1.0 O.D.; the scale was expanded to differentiate the lower intensity bands.

TABLE 10

| CELL LINE | LANE | RELATIVE LEVELS OF cAMP RECEPTOR PROTEINS | | | |
|---|---|---|---|---|---|
| | | RI | RII | RII/RI | % GROWTH |
| MDA-MB-231 | 1, 8-Cl | 0.25 ± 0.03 | 0.15 ± 0.01 | 0.60 | 45 |
| | 2, $N^6$-BENZYL | 0.25 ± 0.03 | 0.07 ± 0.01 | 0.28 | 55 |
| | 3, DI-BUTYRYL | 1.0 ± 0.1 | 0.07 ± 0.01 | 0.07 | 100 |
| | 4, CONTROL | 1.0 ± 0.1 | 0.05 ± 0.01 | 0.05 | 100 |
| LS-174T | 1, 8-Cl | 0.20 ± 0.02 | 0.25 ± 0.02 | 1.25 | 30 |
| | 2, $N^6$-BENZYL | 0.20 ± 0.02 | 0.25 ± 0.02 | 1.25 | 35 |
| | 3, DI-BUTYRYL | 0.80 ± 0.10 | 0.15 ± 0.02 | 0.19 | 85 |
| | 4, CONTROL | 1.0 ± 0.10 | 0.10 ± 0.02 | 0.10 | 100 |

TABLE 11

| Lane | p21 (Relative Level) | % Growth |
|---|---|---|
| 1, Control | 1.0 ± 0.1 | 100 |
| 2, 8-Cl-cAMP (10 μM) | 0.1 ± 0.01 | 43 |
| 3, 8-Cl-adenosine (5 μM) | 1.0 ± 0.1 | 38 |
| 4, DBcAMP (500 μM) | 0.8 ± 0.1 | 80 |

Table 11 shows the densitometric tracings of autoradiograms at A560 nm. The levels of p21 protein are expressed relative to the p21 level in the untreated control cells which is set equal to 1.0 O.D.

The current approach to treating leukemia is to promote cell differentiation rather than cell killing. The site-selective cAMP analogues of the present invention, which are many fold more active in protein kinase activation than the previously studied cAMP analogues, exert a major growth regulatory effect on a spectrum of human leukemic cell lines.

For the experiments described below, the leukemic cell lines used were HL-60 (acute promyelocytic), K-562 (chronic myelocytic), myc-K562 (chronic myelocytic), and Molt-4 (acute T lymphocytic).

The cells were grown in suspension culture in RPMI 1640 medium supplemented with 10% fetal bovine serum, penicillin (50 U/ml), streptomycin (500 μg/mL), 10 mM HEPES buffer, and extra glutamine. For cell growth experiments, cells were treated with cAMP analogues one time at three hours after seeding, and cell counts in duplicate were performed on a Coulter counter 48 and 72 hours later.

Surface antigen analysis of HL-60 cells was performed by flow cytometry using a panel of monoclonal antibodies reactive with either myeloid cells or monocytic cells. Terminal deoxynucleotidyl transferase (TdT) was assayed by an immunoperoxidase method using a TdT fluorescence kit. Western blotting of c-myc protein was performed using c-myc antibody 15206D11 (Scripps Clinic and Research Foundation, LaJolla, Calif.).

A variety of cAMP analogues, modified at either the C-6 or C-8 positions of the adenine moiety at various concentrations, were tested for their growth inhibitory effect on leukemic cell lines, as shown in Table II. Among the C-8 analogues (site 1-selective) tested, 8-Cl-cAMP exhibited the most potency, demonstrating 50% growth inhibition at 5-20 μM concentrations ($IC_{50}$) in all four leukemic cell lines. 8-Br-, 8-methylthio, and 8-methylamino-cAMP were 5 to 20 times less potent than 8-Cl-cAMP. $N^6$-benzyl-cAMP was the most potent of the C-6 analogues (site 2-selective) test with $IC_{50}$ values of 10 to 30 μM $N^6$-benzoyl-cAMP, which is structurally similar to $N^6$-benzyl-cAMP, exhibited $IC_{50}$ values of 40 to 50 μM. DBcAMP, the analogue most commonly used in previous studies, exhibited the least potency, with $IC_{50}$ values of 500 to 1000 μM, and in Molt-4, the 50% growth inhibition could not be obtained. Growth inhibition by the site-selective cAMP analogues was not due to cell killing; the cells were 80% to 90% viable as determined by exclusion of trypan blue dye.

TABLE 12

Effect of Site-Selective cAMP Analogues on Growth of Leukemic Cell Lines

| Cyclic Nucleotide Analogue | cAMP Analogue | Inhibition of Growth $IC_{50}$ (μM) | | | |
|---|---|---|---|---|---|
| | | HL-60 | Molt-4 | K-562 | myc-K562 |
| C-8 | 8-Chloro | 10 | 5 | 20 | 20 |
| | 8-Bromo | 50 | 100 | 100 | 100 |
| | 8-Thiomethyl | 100 | 100 | 100 | 100 |
| | 8-Aminomethyl | 100 | 100 | 100 | 100 |
| C-6 | $N^6$-Benzyl | 20 | 10 | 27 | 30 |
| | $N^6$-Benzoyl | 50 | 40 | 45 | 50 |
| | $N^6,O^{2'}$-Dibutyryl | 500 | —* | 1,000 | 1,000 |

*No growth inhibition.

Phosphodiesterase inhibitor, such as theophylline (0.1 mM) or 1-methyl-3-isobutylxanthine (0.5 mM), each alone had little or no growth inhibitory effect, and the inhibitors could not enhance the analogue effect when added in combination with the analogue. These results suggest that the analogues produced growth inhibition at concentrations below which the degradation by phosphodiesterase could take place, and also that the growth inhibition was not due to raising cellular cAMP.

The effect of site-selective cAMP analogues on the expression of differentiation markers in HL-60 cells was examined to determine if the growth-arrested HL-60 cells were more differentiated than the untreated cells. Treatment for three days with 8-Cl-cAMP exhibiting 90% viability induced a marked increase in the expression of monocyte-specific surface antigens (MO2, OKM5) and a decrease in markers related to immature progenitor cells (My7, My9), cf. Table 13.

TABLE 13

Modulation of Differentiation Markers in HL-60 Cells by 8-Cl-cAMP

| Markers | Control | 8-Cl-cAMP* (20 μM) |
|---|---|---|
| | % Positive | |
| My7 | 81 | 11 |
| My9 | 75 | 54 |
| Leu M1 | 72 | 0 |
| Leu M5 | 0 | 0 |
| MO$_2$ | 0 | 75 |
| OKM5 | 0 | 51 |

*Seventy percent growth inhibition with 90% cell viability.

Disappearance of cellular TdT has been considered as a differentiation marker for human T lymphocytic leukemia. Treatment of Molt-4 (acute T lymphocytic) leukemia cells with 8-Cl-cAMP (10 μM) caused a time-dependent decrease in TdT activity; at two days after the treatment, TdT activity decreased to 50% of that in untreated control cells, and by day 4, the activity decreased to 10% of the untreated control levels. Moreover, treatment for four days with 8-Cl-cAMP in combination with $N^6$-benzyl cAMP (20 μM) caused almost complete loss (>95%) of TdT activity. These cells exhibiting the loss of TdT demonstrated >90% viability.

A propidium iodide staining method was used to determine if the reason for reduced cell proliferation observed in the leukemic cell lines after treatment with the analogues was due to a specific block in one phase of the cell cycle. The results showed that the fractions of cells in each phase of the cell cycle were not appreciably different between the control cells and the cells treated with the analogues.

The type I isozyme of cAMP-dependent protein kinase has been considered to be involved in cell proliferation and transformation, whereas the type II isozyme is involved in cell differentiation and inhibition of cell growth. Because type I and type II protein kinase differ only in their regulatory subunits, the cAMP binding receptor protein, the cAMP receptor protein was measured during the analogue treatment of these leukemic cells, using the photoaffinity ligand 8-$N_3$-[$^{32}$P]cAMP. As shown in FIG. 9A, the untreated Molt-4 leukemic cells contained a major cAMP receptor protein with a molecular weight of 48,000 (lane 1), the RI cAMP receptor protein (the regulatory subunit of type I protein kinase). When the cells were treated for three days with 8-Cl-cAMP (lane 2), the RI receptor protein markedly decreased, whereas the RI protein remained without appreciable change when the cells were treated with DBcAMP (lane 3). That the decrease of the RI receptor photoaffinity labelling found after 8-Cl-cAMP treatment could be due to the presence of bound 8-Cl-cAMP to the RI receptor is unlikely; 8-Cl-cAMP, like 8-piperidino-cAMP, selectively binds to site 1 of RII but binds to site 2 of the RI receptor. Thus, 8-Cl-cAMP bound to site 2 of RI would synergistically enhance, instead of interfering with, the site 1-selective binding of 8-$N_3$-[$^{32}$P]-cAMP.

The 8-Cl-cAMP also caused a marked reduction of c-myc protein level, as shown in FIG. 9B, lane 2, whereas DBcAMP, lane 3, did not affect the c-myc protein level, indicating that a decrease in RI and c-myc protein levels caused by 8-Cl-cAMP treatment does not merely reflect growth inhibition or cell death in general. A similar decreases in RI and c-myc protein levels also occurred in other leukemic lines, K-562, myc-K562, and HL-60, after 8-Cl-cAMP treatment. The RII cAMP receptor protein was not detected in Molt-4, but was measurable in other leukemic cell lines. The analog treatment did not affect the RII levels in these leukemic cells.

In FIG. 9, A shows the photoactivated incorporation of 8-$N_3$-[$^{32}$P]-cAMP; B shows the Western blotting of c-myc protein; RII, the 56,000 molecular weight RII CAMP receptor protein; c-myc protein, a purified preparation of c-myc protein. Lane 1, untreated control cells; lanes 2 through 4, the cells treated for three days with 5 μM of 8-Cl-cAMP, DBcAMP (1mM), and 8- Cl-adenosine (5 μM), respectively. M, marker proteins of known molecular weight. Each lane contained 100 micrograms protein for sodium dodecyl sulfate-polyacrylamide gel electrophoresis (SDS-PAGE). The cell pellets, after two washes with phosphate-buffered saline, were suspended in buffer ten (0.1 mol/L NaCl, 5 mM MgCl2, 1% Nonidet P-40, 0.5% Na deoxycholate, 2 KIU/mL bovine aprotinin, 20 mM Tris-HCl, pH 7.4) (2×10$^7$ cells/mL) vortexed, passed through a 22-gauge needle ten times, allowed to stand for 30 minutes at 4° C., and centrifuged at 750×g for 20 minutes at 4° C. The resulting supernatants were used as cell lysates. The numbers in the panel represent the average value ±SE of seven separate experiments. ND=nondetectable.

As described above, the cAMP analogues of the present invention were shown to exert a major effect on the growth of promyelocytic, chronic myelocytic, and acute T lymphocytic human leukemic cell lines at micromolar concentrations. The analogue effect was not due to raising of cellular cAMP levels as was previously believed, because phosphodiesterase inhibitors in combinations with the analogue did not enhance the analogue effect. The analogues worked directly through cAMP receptor protein, the regulatory subunit of cAMP-dependent protein kinase. Among the site-selective analogues tested, 8-Cl-cAMP exhibited the most potency. The analogue effect correlated with a selective modulation of two types of cAMP receptor proteins—a marked reduction in the RI receptor, which was previously related to cell growth and transformation, with no change in the RII receptor, which was related to growth arrest and differentiation.

This selective modulation of the RI and the RII cAMP receptor protein was not achieved by the early-known analogue, DBcAMP. The growth inhibition also caused a marked reduction in c-myc protein level. The decrease in the RI cAMP receptor and c-myc protein level was not observed when cells were growth arrested by 8-Cl-adenosine, indicating that the analogue effect was not due to its adenosine metabolite.

The growth arrest by the analogues accompanied differentiation of the leukemic cells, as shown by the expression of several surface antigens specific for monocytic differentiation in HL-60 cells and a loss of the activity of TdT, a marker enzyme for cell immaturity in Mold-4 cells. Despite the appearance of markers of mature phenotype and definitive growth arrest shown in the analogue-treated cells, the cell cycle phase distribution between the treated and untreated cells was similar.

In normal myeloid cell precursors, the growth inducers induce cell viability and cell multiplication and also production of differentiation inducers. In leukemic cells, therefore, continuous production of growth inducers may be essential for continuous production of differentiation inducers to achieve their terminal differentiation. The site-selective cAMP analogues, which produce growth arrest while allowing the cells to progress through their normal cell cycle but at a slower rate, may terminally differentiate leukemic cells because these agents allow continuous production of differentiation inducers. Thus, the site-selective cAMP analogues of the present invention restore the balance between proliferation and maturation of leukemic cells.

It has been shown also that the synergism of growth inhibition by C-6 analogues when combined with 8-thio or 8-halogen analogues far exceeds that by C6 analogues in combinations with 8-amino derivatives. This suggests a response of type II rather than type I protein kinase. In fact, an increase in the RII cAMP receptor protein with a decrease in the RI receptor protein observed during growth inhibition correlated with the growth inhibitory potency of the analogues, cf. FIG. 5 and 6. This unique behavior of the site-selective analogues demonstrating selective modulation of the RI and RII cAMP receptor proteins in cancer cells is not mimicked by the earlier known analogue, cAMP itself, or agents that increase cellular cAMP levels. cAMP at high levels, having no site selectivity, activates both type I and type II protein kinase isozymes maximally and equally without discrimination.

Because the site-selective cAMP analogues in combination brought about a synergistic effect, the combination permitted the use of lower total analogue concentration to achieve the same growth inhibitory effect as would be obtained using a single analogue. Thus, the site-selective analogues in combination exerted the growth inhibition at concentrations at least one-tenth below the reported I50 for the low Km cAMP phosphodiesterase. At these low concentrations, the analogues would not be metabolized to produce their toxic adenosine analogues. If fact, by HPLC analysis, 8-Cl-adenosine was not detected in the cell extracts or medium after treatment of cells for 48–72 hours with 8-Cl-cAMP at a concentration as high as 50 µM. A role for 8-Cl-adenosine toxicity in the inhibition of cell growth was further excluded by the experimentation that showed the different behavior between 8-Cl-cAMP and 8-Cl-adenosine in cell cycle effect, release from growth inhibition, and modulation of p21 ras protein. Thus, the growth inhibitory effect of the site-selective compounds described herein clearly differs from that in previous reports that have shown strong cytotoxicity lethal to the rat hepatoma cells using some of the amino-substituted C-8 analogues and cyclic nucleotides of purine analogues.

Growth inhibition by the compounds of the present invention accompanied biochemical and morphological changes but did not produce $G_1$ arrest in the cancer cells tested. It appears therefore, that the compounds of the present invention produce growth inhibition by slowing down the cell cycle progression and perhaps promoting cell differentiation. In fact, a role of site-selective cAMP analogues in promotion of differentiation has been shown in leukemic cell lines.

The following examples serve to further illustrate the present invention but are not intended to limit the scope of the invention.

EXAMPLE 1

This example describes a method of cell culture used in the study of derivatives of cAMP analogues.

HL-60 leukemic cells were obtained from the American Type Culture Collection (Rockville, Md.) and were grown in suspension culture in RPMI 1640 supplemented with 10% heat-inactivated fetal bovine serum, streptomycin (500 µg/ml), penicillin (50 units/ml), and glutamine (1 mM) (Gibco, Grand Island, N.Y.).

LS-174T human colon carcinoma cells were obtained from the National Cancer Institute, Division of Cancer Treatment, Bethesda, Md., and were grown in Eagle's minimum essential medium supplemented with 10% heat-inactivated fetal bovine serum, Eagle's minimum essential medium nonessential amino acids, 20 mM 4-(2-hydroxyethyl)-1-piperazineethanesulfonic acid, 2mM glutamine, and penicillin-streptomycin (Gibco). The medium was changed every 48 hours.

EXAMPLE 2

This example describes the binding affinities of Rp- and Sp- analogues of cAMP. 8-chloro-adenosine 31:51-monophosphate (8-Cl-cAMP) was obtained from the National Cancer Institute, Division of Cancer Treatment, Bethesda, Md. 8-bromo-adenosine 3': 5'-monophosphate (8-Br-cAMP) was obtained from Sigma Chemical Company, St. Louis, Mo. Rp- (equatorial exocyclic sulfur substitution) and Sp- (axial exocyclic sulfur substitution) 8-chloro-adenosine 3': 5'-monophosphorothioate (cAMPS) and -cAMPS analogues were synthesized as described in O'Brian et al. (Biochemistry 21: 4371–4376 (1982)), Dostmann (Ph.D. dissertation, Universitat Bremen, Germany, 1987), and Genieser et al. (Tetrahedron Lett. 19: 2803–2804 (1988)).

The affinities of the cAMP analogues for Site A (Site 2) and Site B (Site 1) of RI and RII were determined and standardized against the relative affinity of cAMP for the same sites in accordance with the following formula:

$$K_i \text{ (analogue)} = \frac{K_i \, cAMP}{K_i \, \text{analogue}}$$

TABLE 14

Binding affinity of Sp- and Rp- and cyclophosphate analogues of cAMP for cAMP receptor proteins, RI and RII RI and RII are the regulatory subunits of cAMP-dependent protein kinase type I and type II, respectively. Site A (Site 2) and Site B (Site 1) are two distinct cAMP binding sites on cAMP receptor proteins (RI and RII): the affinities of analogues for Site A and Site B were determined by the measurement of kinetic constants (inhibition constant, $K_i$), and the values are expressed as the relative affinity $K_i$ (cAMP)/$K_i$ (analogue), i.e., the ratio between the apparent inhibition constant for cAMP and the analogue, as described in Ogreid et al., Eur. J. Biochem. 150:219–227 (1985).

|  | RI | | RII | |
| --- | --- | --- | --- | --- |
| Analogue | Site A | Site B | Site A | Site B |
| Sp-8-Cl-cAMPS | 0.18 | 0.037 | 0.0023 | 2.4 |
| Rp-8-Cl-cAMPS | 0.0079 | 0.0042 | 0.00028 | 0.44 |
| Sp-8-Br-cAMPS[a] | 0.19 | 0.054 | 0.003 | 2.2 |
| 8-Cl-cAMP[b] | 2.71 | 2.0 | 0.051 | 4.61 |
| 8-Br-cAMP[c] | 1.30 | 1.0 | 0.11 | 6.8 |

[a]Dostmann et al., J. Biol. Chem., 265: 10484–10491 (1990).
[b]Ally et al., Proc. Natl. Acad. Sci. USA. 85: 6319–6322 (1988).
[c]Ogreid et al., Eur. J. Biochem. 181: 19–31 (1989).

As shown in Table 14, both Sp-8-Cl-cAMPS and Sp-8-Br-cAMPS exhibited a greater decrease in affinity for Site B (54- and 19-fold decrease, respectively) than Site A (15- and 7-fold decrease, respectively) of RI, while showing preferential decrease in affinity for Site A (22- and 37-fold decrease, respectively) over Site B (1.9- and 3.1-fold decrease, respectively) of RII as compared with the corresponding cyclophosphate. Rp-8-Cl-cAMPS exhibited a 340- and 480-fold decrease in affinity for Site A and B, respectively, of RI and a 180-fold decrease in affinity for Site A of RII as compared with its cyclophosphate, 8-Cl-cAMP. However, Site B of RII showed the smallest reduction (a 10-fold decrease). Thus, a greater decrease in affinity for Site B than for Site A of RI and a substantial decrease in affinity for Site A of RII with a small decrease in the Site B affinity of RII are the common changes resulting from the modifications of 8-Cl-cAMP.

The protein kinase activation constants ($K_a$) of the Sp- and Rp-cAMPS were determined by measuring the transfer of 32p from [γ-$^{32}$P] ATP to Kemptide as described by Ogreid et al., Eur. J. Biochem. 150: 219–227 (1985).

TABLE 15

Activation potency of Sp- and RP-8-Ci-cAMPS and 8-Cl-cAMP for protein kinase
Protein kinases types I (cAKI) and II (cAKII) were prepared from rabbit skeletal muscle and bovine heart, respectively, as described in Døskeland et al. (J. Biol. Chem. 259: 2291–2301 (1984)). $K_a$ is the concentration of cAMP or analogue sufficient for half-maximum activation of the protein kinase in Ogreid et al. (Eur. J. Biochem. 150: 219–227 (1985)). U. M.: unmeasurable.

| Analogue | Activation Constant ($K_a$) cAKI | cAKII |
|---|---|---|
| Sp-8-Cl-cAMPS | $2.5 \times 10^{-7}$ | $2.5 \times 10^{-7}$ |
| Rp-8-Cl-cAMPS | U. M. | U. M. |
| 8-Cl-cAMPS | $1.8 \times 10^{-8}$ | $1.0 \times 10^{-7}$ |
| cAMP | $4.0 \times 10^{-8}$ | $8.0 \times 10^{-8}$ |

As shown in Table 15, Sp-8-Cl-cAMPS had an 11- and a 2.5-fold increase in the $K_a$ for protein kinase type I and type II, respectively, as compared with 8-Cl-cAMP.

EXAMPLE 3

This example describes the inhibition of the growth of HL-60 cells by derivatives of cAMP analogues.

HL-60 cells were seeded at a density of $2 \times 10^5$/ml and treated with the cAMP analogues 3 hours after seeding. Cell counts were performed at desired times on a Coulter Counter. The derivatives of cAMP analogues were tested for their growth-inhibitory effect on HL-60 leukemia cells in comparison with their homologous cyclophosphate derivatives.

As shown in FIG. 1, 8-Cl-cAMP is a potent growth inhibitor of HL-60 cells. Rp-8-Cl-cAMPS was less inhibitory than 8-Cl-cAMP but was more potent than Sp-8-Cl-cAMPS. The growth inhibitory effect of 8-Br-cAMP was low (<5% growth inhibition at 20 μM). However, a marked enhancement of growth inhibition was observed with Sp-8-Br-cAMPS (47% growth inhibition at 20 μM). The growth inhibitory effect of Rp- and Sp-cAMPS was negligible (<5% at 20 μM).

TABLE 16

Growth inhibition of HL-60 human leukemia cells by derivatives of cAMP analogues
The IC$_{50}$ values were determined from the dose-response curve experiments like those shown in FIG. 1 and represent an average value obtained for each analogue from two or more separate experiments carried out from 3 days or 6 days. Initial cell number, $1 \times 10^5$/dish. Typical numbers of untreated control cells at day 3 and day 6 were 265,000 and 1,011,840, respectively. 99% cell viability in treated and control cells.

| | Growth inhibition (IC$_{50}$) (μM) | |
|---|---|---|
| Analogue | Day 3 | Day 6 |
| Rp-8-Cl-cAMPS | 16 | 3 |
| Sp-8-Cl-cAMPS | 100 | 8 |
| Sp-8-Br-cAMPS | 28 | 3 |
| 8-Br-cAMP | 100 | 18 |
| 8-Cl-cAMP | 5 | 0.4 |

The concentrations of cAMP analogues that inhibit 50% of cell proliferation (IC$_{50}$) are shown in Table 16. The IC$_{50}$ values of all of the analogues at day 6 were 10- to 12-fold lower than those at day 3, indicating that the sensitivity of cells to analogues increased with the length of time of treatment. The IC$_{50}$ values of day 6 indicate that the Rp- and Sp-phosphorothioates of 8-Cl-cAMP were 10- and 20-fold less potent, respectively, than 8-Cl-cAMP. In contrast, Sp-8-Br-cAMPS, which exhibited the same IC$_{50}$ value as that of Rp-8-Cl-cAMPS, was 6-fold more potent than 8-Br-cAMP.

In order to determine if the reduction in cell proliferation that was observed in HL-60 cells was due to a specific block in one phase of the cell cycle, cells were stained using a propidium iodide staining method as described by Pepe et al. (Cancer Res. 51: 6263–6267 (1991)), Braylan et al. (Cytometry 2: 337–343 (1982)), and Neckers et al. (Mol. Cell. Biol. 6: 4244–4250 (1986)). Briefly, cells were fixed in 70% ethanol and stored at 4° C. before analysis. Nuclear DNA was stained with propidium iodide, 50 μg/ml in phosphate-buffered saline (pH 7.4), for 30 minutes at room temperature. RNase was added to avoid double-helix RNA staining. The DNA content of cells was analyzed by a FACScan flow cytometer coupled with a Hewlett-Packard computer. Cell cycle data analysis was performed by a Cell-FIT program according to the method of Dean (Cell Tissue Kinet. 13: 299–308 (1980)) (Becton Dickinson Immunocytometry Systems). Pulse area versus pulse width gating was performed to exclude doublets from the G$_2$-M region. For each sample, 20,000 events were stored in list mode. Cell surface antigen analysis was performed by flow cytometry with FACScan using a panel of monoclonal antibodies reactive with either monocytic or myeloid cells.

TABLE 17

Effect of Rp and Sp-8-Cl-cAMPS on cell cycle kinetics of HL-60 cells after 96 hours of treatment.

| Treatment | % G$_0$–G$_1$[a] | % S | % G$_2$M |
|---|---|---|---|
| Control | 45.7 | 46 | 8.3 |
| Rp-8-Cl-cAMPS, 10 μM | 43.5 | 46.7 | 9.8 |
| Rp-8-Cl-cAMPS, 50 μM | 41.6 | 49.4 | 9.0 |
| Rp-8-Cl-cAMPS, 100 μM | 37.9 | 51.2 | 10.9[b] |
| Sp-8-Cl-cAMPS, 10 μM | 46.8 | 44.3 | 8.9 |
| Sp-8-Cl-cAMPS, 50 μM | 46 | 45.4 | 8.6 |

TABLE 17-continued

Effect of Rp and Sp-8-Cl-cAMPS on cell cycle
kinetics of HL-60 cells after 96 hours of treatment.

| Treatment | % $G_0$–$G_1$[a] | % S | % $G_2M$ |
|---|---|---|---|
| Sp-8-Cl-cAMPS, 100 μM | 56 | 35 | 9.0 |
| 8-Cl-cAMPS, 5 μM | 35.8 | 52.8 | 11.3 |
| $N^b$-Benzyl-cAMP, 10 μM | 44.4 | 46 | 9.6 |

[a]Coefficiency of variation of $G_0$–$G_1$ = 2.1 ~ 2.9.
[b]Toxic effect.

As shown in Table 17, the fractions of cells in $G_1$, S, and $G_2$-M phases were not appreciably different between control cells (untreated) and those treated with Rp- or Sp-8-Cl-cAMPS for 96 hours.

EXAMPLE 4

This example describes the inhibition of the growth of LS-174T human colon carcinoma cells by phosphorothioates of cAMP analogues.

LS-174T cells were seeded at a density of $2 \times 10^5$ /60 mm dish. The medium was removed 24 hours later and fresh medium containing cAMP analogues was added, using 100×concentrated stock solutions. At desired times, cell counts were performed in duplicate on a Coulter Counter after harvesting cells with gentle trypsinization. The phosphorothioate derivatives of cAMP analogues were tested for their growth-inhibitory effect in LS-174T colon carcinoma cells in comparison with their homologous cyclophosphate derivatives.

TABLE 18

Effect of phosphorothioate derivatives of cAMP
analogues on the growth of LS-174T human
colon carcinoma cells
The percentage growth inhibition values shown at 10
and 50 μM analogue concentrations were determined from
the dose-response curve experiments like those shown in
FIG. 1 and represent an average value obtained for each
analogue from two or more separate experiments. Sp-6-SET-
cPMPS: Sp-6-ethylthiopurine-3':5'-monophosphorothioate;
Sp-2-Cl-cAMPS: Sp-2-Chloroadenosine-3':5'-
monophosphorothioate.

| | % Growth inhibition at | |
|---|---|---|
| | 10 μM | 50 μM |
| Rp-8-Cl-cAMPS | 48 | 70 |
| Sp-8-Br-cAMPS | 40 | 60 |
| Sp-6-SET-cPMPS | 25 | 50 |
| Sp-8-Cl-cAMPS | 20 | 40 |
| Rp-cAMPS | 15 | 35 |
| Sp-2-Cl-cAMPS | 10 | 25 |
| Sp-cAMPS | 7 | 15 |

As shown in Table 18, Rp-8-Cl-cAMPS and Sp-8-Br-cAMPS exhibited the greatest inhibition of cell growth. Sp-6-SETcPMPS, Sp-8-Cl-cAMPS, and Rp-cAMPS showed moderate potency. Sp-cAMPS and Sp-2-Cl-cAMPS exhibited the least potency.

TABLE 19

Additive growth inhibitory effect between
phosphorothioate analogue and 8-Cl-cAMP on LS-174T human
colon carcinoma cells
The percentage growth inhibition values represent an
average value obtained from two separate experiments
carried out for 4 days. The analogues were added at 24
hours after seeding.

| Compound | Concentration (μM) | % Growth inhibition LS-174T |
|---|---|---|
| Rp-8-Cl-cAMpS | 5 | 34 |
| | 10 | 48 |
| | 200 | 80 |
| 8-Cl-cAMp | 1 | 30 |
| Rp-cAMPS | 50 | 35 |
| Rp-8-Cl-cAMpS | 5 | 68 |
| + | | |
| 8-Cl-cAMp | 1 | |
| Rp-8-Cl-cAMPS | 10 | 75 |
| + | | |
| 8-Cl-cAMp | 1 | |
| Rp-8-Cl-cAMPS | 200 | 83 |
| + | | |
| 8-Cl-cAMp | 1 | |
| Rp-cAMPS | 50 | 67 |
| + | | |
| 8-Cl-cAMP | 1 | |

As shown in Table 19, neither Rp-8-Cl-cAMPS nor Rp-cAMPS interfered with the growth-inhibitory effect of 8-Cl-cAMP. Both exhibited an additive effect.

EXAMPLE 5

This example describes the differentiation of HL-60 leukemia cells by Rp-8-Cl-cAMPS.

The effect of Rp- and Sp-8-Cl-cAMPS on the expression of differentiation markers in HL-60 cells was examined to determine if the growth-arrested HL-60 cells are more differentiated than untreated cells. Control (untreated) cells and cells treated with cAMP analogues for 96 hours were analyzed for the expression of monocyte (Leu-M3, HLA-DR, and Leu-15) and myeloid (Leu-M1) specific antigens. For each sample, $2 \times 10^4$ cells were analyzed. Cell surface antigen analysis was performed by flow cytometry with FACScan. Cell gating was performed using forward and side scatter.

As shown in FIG. 2, cells treated for 3 days with 50 μM Rp-8-Cl-cAMPS showing a 90% cell viability exhibited an increase in the expression of monocyte-specific surface antigens (3- and 2-fold increase of Leu-15 and HLA-DR, respectively, over the control cell levels) as did 5 μM 8-Cl-cAMP, whereas treatment of cells with 100 μM Sp-8-Cl-cAMPS had no appreciable effect on the surface antigen expression. A synergistic effect on the surface antigen expression was observed for Rp-8-Cl-cAMPS in combination with $N^6$-benzyl-cAMP (10- and 6-fold increase of Leu-15 and HLA-DR, respectively, over the control cell levels). These results show that Rp-8-Cl-cAMPS can mimic the effect of 8-Cl-cAMP on the differentiation of HL-60 leukemia cells.

Diastereomeric phosphorothioates of cAMP analogues have been shown to be potent inhibitors of the growth of human cancer cell lines. Rp-8-Cl-cAMPS and Sp-8-Br-cAMPS, both of which exhibit $IC_{50}$ of 3 μM in HL-60 leukemia cells, are the two most potent growth inhibitors among the phosphorothioates tested. The growth inhibitory effect of Rp-8-Cl-cAMPS was about 10-fold lower than that of 8-Cl-cAMP but 3-fold greater than that of Sp-8-Cl-cAMPS. The mechanism of action of Rp-8-Cl-cAMPS in growth inhibition appears to be similar to that of 8-Cl-cAMP. Rp-8-Cl-cAMPS did not bring about any change in cell cycle phase like 8-Cl-cAMP (Tortora et al., Blood 71: 230–233 (1988)). Rp-8-Cl-cAMPS enhanced its growth inhibitory effect when in combination with 8-Cl-cAMP and increased its cell differentiation effect when in combination with $N^6$-benzyl-cAMP like 8-Cl-cAMP in combination with $N^6$-benzyl-cAMP (Tortora et al., PNAS USA 86: 2849–2852 (1989)).

The striking potency of 8-Cl-cAMP in growth inhibition has been related to its selective bifunctional effect on protein kinase isozyme type I versus type II. It drastically down-regulates type I protein kinase by dissociating it into its subunits while upregulating type II protein kinase in its holoenzyme form (Ally et al., PNAS USA 85: 6319–6322 (1988); Cho-Chung, Cancer Res. 50: 7093–7100 (1990)).

Rp derivatives of cAMP or analogues of cAMP, such as 8-Cl-cAMP, exhibited an agonistic effect on growth inhibition. In general, Sp and Rp modifications render cAMP analogues more lipophilic and resistant to hydrolysis by phosphodiesterase (PDE). Accordingly, although 8-Cl-cAMP, for example, may be more potent than its Rp derivative, the fact that it is subject to PDE hydrolysis makes it a less desirable candidate in practical applications, such as chemotherapy, where the hydrolysis of the compound would result in the generation of toxic metabolites. In contrast, the Rp derivative is not subject to hydrolysis. However, it demonstrates a lower affinity for binding to the cAMP protein kinase and, consequently, would necessitate the administration of larger doses. Accordingly, the use of 8-Cl-cAMP in combination with Rp-8-Cl-cAMPS, whether administered simultaneously, sequentially, or alternately in a repetitive sequence, would provide a solution to effective inhibition of abnormal cellular growth, such as that characteristic of cancerous or leukemic cells, in clinical applications, such as chemotherapy.

The site-selective analogues of the present invention were able to arrest the growth of cancer cells that are resistant to comparable levels of DBcAMP. Thus, the site-selective cAMP analogues of the present invention are useful as a biological tool in the growth control of a wide spectrum of cancer cells, including those previously found to be resistant to other cAMP analogues or to agents that increase intracellular cAMP.

The compounds of the present invention are administered in amounts such as to provide a concentration of from about 0.1 to about 100 $\mu M$ in the serum of the patient. The compounds may be administered in a variety of ways, including via osmotic pump, pellet implantation, or other method that may provide a continuous supply of the compound.

The compounds of the present invention may be administered in effective amounts in a variety of ways contained in a pharmaceutically acceptable carrier. Compositions within the scope of the invention include compositions wherein the compounds are contained in an effective amount to achieve the intended purpose. Determination of the effective amounts is within the skill in the art.

In addition to the cAMP analogue or combination of cAMP analogues and pharmaceutically acceptable salts thereof of the present invention, the pharmaceutical compositions may contain suitable pharmaceutically acceptable carriers comprising excipients and auxiliaries which facilitate processing of the active compounds into preparations which can be used pharmaceutically. Preferably, the preparations, particularly those which can be administered orally and which can be used for the preferred type of administration, such as tablets, dragees, and capsules, and also preparations which can be administered rectally, such as suppositories, as well as suitable solutions for administration by injection or orally, contain from about 0.1 to 99 percent, preferably from about 25 to 85 percent by weight of active ingredient, together with the excipient.

The pharmaceutical compositions of the present invention are manufactured in a known manner, for example, by means of conventional mixing, granulating, dragee-making, dissolving, or lyophilizing processes. Thus, pharmaceutical preparations for oral use can be obtained by combining the active compounds with solid excipients, optionally grinding a resulting mixture and processing the mixture of granules, after adding suitable auxiliaries, if desired or necessary, to obtain tablets or dragee cores.

Suitable excipients are, in particular, fillers such as sugars, for example, lactose, sucrose, mannitol, or sorbitol; cellulose preparations; and/or calcium phosphates, such as tricalcium phosphate or calcium hydrogen phosphate, as well as binders such as starch paste, using, for example, rice starch, corn starch, wheat starch, potato starch; gelatin, gum tragacanth, methyl cellulose, hydroxypropylcellulose, sodium carboxymethylcellulose, and/or polyvinylpyrrolidone. If desired, disintegrating agents may be added, such as the above-mentioned starches and carboxymethyl starch, crosslinked polyvinyl pyrrolidone, agar, or alginic acid or a salt thereof such as sodium alginate.

Auxiliaries include, above all, flow-regulating agents and lubricants, such as silica gel, talc, stearic acid and salts thereof such as magnesium stearate or calcium stearate, and/or polyethylene glycol. Dragee cores are provided with suitable coatings which, if desired, may be resistant to gastric juices. For the purpose, concentrated sugar solutions may be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations such as acetyl-cellulose phthalate or hydroxypropylmethyl-cellulose phthalate, are used. Dyestuffs and pigments may be added to the tablets or dragee coatings, for example, for identification or in order to characterize different combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, liquid paraffin, or liquid polyethylene glycols. In addition, stabilizers may be added.

Possible pharmaceutical preparations which can be used rectally include, for example, suppositories which consist of a combination of the active compounds with a suppository base. Suitable suppository bases are, for example, natural or synthetic triglycerides, paraffin hydrocarbons, polyethylene glycols, or higher alkanols. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble or -dispersible form. These water-soluble or water-dispersible forms may be as pharmaceutically acceptable salts of the analogues, such as sodium, potassium, calcium, magnesium, and like salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension, such as sodium carboxymethyl cellulose, sorbitol, and/or dextran. Optionally, the suspension may also contain stabilizers.

The active ingredients may also be administered as liposomes, pharmaceutical compositions in which the active ingredient is contained either dispersed or variously present in corpuscles consisting of aqueous concentric layers adherent to lipidic layers (hydrophobic). The drug may be present both in the aqueous layer and in the lipidic one (inside or outside), or, in any event, in the non-homogeneous system generally known as a liposomic suspension.

The hydrophobic layer, generally but not exclusively, comprises phospholipids such as lecithin and sphingomycelin, steroids such as cholesterol, more or less ionic surface-active substances such as diacetylphosphate, stearylamine or phasphatidic acid, and/or other materials of the hydrophobic nature.

The use of derivatives of cAMP to treat cancer cells is described in detail in U.S. patent application Ser. No. 07/198,489, filed on May 23, 1988. The disclosure of that application is hereby incorporated in its entirety by reference.

While the invention is described above in relation to certain specific embodiments, it will be understood that many variations are possible, and that alternative materials and reagents can be used without departing from the invention. In some cases such variations and substitutions may require some experimentation, but such will only involve routine testing.

The foregoing description of the specific embodiments will so fully reveal the general nature of the invention that others can, by applying current knowledge, readily modify and/or adapt for various applications such specific embodiments without departing from the generic concept, and therefore such adaptations and modifications are intended to be comprehended within the meaning and range of equivalents of the disclosed embodiments. It is to be understood that the phraseology or terminology herein is for the purpose of description and not of limitation.

While the invention has been described with an emphasis upon preferred embodiments, it will be obvious to those of ordinary skill in the art that variations in the preferred methods, compounds, and compositions can be used and that it is intended that the invention can be practiced otherwise than as specifically described herein. Accordingly, this invention includes all modifications encompassed within the spirit and scope of the invention as defined by the appended claims.

What is claimed is:

1. A method of inhibiting neoplastic cellular growth, which method comprises contacting neoplastic cells with an effective neoplastic cellular growth inhibiting amount of a compound selected from the group consisting of phosphorothioate derivatives of cAMP analogues, wherein said cAMP analogues have been modified at either or both the $N^6$ or C-8 positions of the adenine moiety, wherein said $N^6$- or C-6 substitution is selected from the group consisting of monobenzyl, monoethoxycarbonyl, monobenzoyl, monophenylcarbamoyl, monobutyryl, monophenyl, and diethyl or N-piperidino, and wherein said C-8 substituent is selected from the group consisting of halogen, methylthio, p-chlorophenylthio, β-hydroxyethylamino and methylamino, and pharmaceutically acceptable salts thereof.

2. The method of claim 1, wherein said compound is a phosphorothioate derivative of an 8-halo-cAMP.

3. The method of claim 2, wherein said compound is a phosphorothioate derivative of 8-Cl-cAMP, 8-Br-cAMP, or 8-I-cAMP.

4. The method of claim 3, wherein said compound is selected from the group consisting of Rp-8-Cl-cAMPS and Sp-8-Br-cAMPS.

5. The method of claim 4, wherein said compound is Rp-8-Cl-cAMPS.

6. The method of claim 5, wherein said compound is in a pharmaceutically acceptable carrier.

7. The method of claim 1, which further comprises contacting said cells with an effective amount of an additional compound selected from the group consisting of 8-Cl-cAMP, $N^6$-benzyl-cAMP, $N^6$-benzoyl-8-methylthio-cAMP, 8-methylthio-cAMP, $N^6$-benzoyl-cAMP, 8-bromo-cAMP, 8-iodo-cAMP, 8-p-chlorophenyl-thio-cAMP, 8-β-hydroxyethylamino-cAMP, 8-methylamino-cAMP, 8-N,N-dimethylamino-cAMP, $N^6$-phenylcarbamoyl-cAMP, $N^6$-butyryl-cAMP, $N^6$-phenyl-8-p-chlorophenylthio-cAMP, $N^6,N^6$-diethyl-8-p-chlorophenylthio-cAMP, 6-piperidino-8-p-chlorophenylthio-cAMP, $N^6$-benzyl-8-benzylthio-cAMP, $N^6$-ethoxycarbonyl-cAMP, $N^6$-n-butyl-8-p-chlorophenylthio-cAMP, pharmaceutically acceptable salts thereof, and mixtures thereof.

8. The method of claim 7, wherein said additional compound is selected from the group consisting of 8-Cl-cAMP and pharmaceutically acceptable salts thereof.

9. The method of claim 8, wherein said cells are contacted with said compounds simultaneously.

10. The method of claim 9, wherein said compounds are combined in a single pharmaceutical composition.

11. The method of claim 8, wherein said cells are sequentially contacted with said compounds.

12. The method of claim 7, wherein said additional compound is selected from the group consisting of $N^6$-benzyl-cAMP and pharmaceutically acceptable salts thereof.

13. The method of claim 12, wherein said compounds act to increase cell differentiation.

14. The method of claim 1, wherein said cells have more $RI_\alpha$ isoform than $RII_\beta$ isoform of the cAMP receptor protein.

15. The method of claim 1, wherein said cells are cancerous.

16. The method of claim 1, wherein said cells are leukemic.

17. The method of claim 1, wherein said compound antagonizes cAMP-dependent protein kinases in vivo.

18. A pharmaceutical composition comprising a compound selected from the group consisting of phosphorothioate derivatives of cAMP analogues, wherein said cAMP analogues have been modified at either or both the $N^6$ or C-8 positions of the adenine moiety, wherein said $N^6$- or C-6 substitution is selected from the group consisting of monobenzyl, monoethoxycarbonyl, monobenzoyl, monophenylcarbamoyl, monobutyryl, monophenyl, and diethyl or N-piperidino, and wherein said C-8 substituent is selected from the group consisting of halogen, methylthio, p-chlorophenylthio, β-hydroxyethylamino and methylamino, and pharmaceutically acceptable salts thereof, and a pharmaceutically acceptable carrier.

19. The pharmaceutical composition of claim 18, wherein said compound is a phosphorothioate derivative of 8-halo-cAMP.

20. The pharmaceutical composition of claim 19, wherein said compound is a phosphorothioate derivative of 8-Cl-cAMP, 8-Br-cAMP, or 8-I-cAMP.

21. The pharmaceutical composition of claim 18, wherein said compound is selected from the group consisting of Rp-8-Cl-cAMPS and Sp-8-Br-cAMPS.

22. The pharmaceutical composition of claim 21, wherein said compound is Rp-8-Cl-cAMPS.

23. The pharmaceutical composition of claim 18, which further comprises an additional compound selected from the group consisting of 8-Cl-cAMP, $N^6$-benzyl-cAMP, $N^6$-benzoyl-8-methylthio-cAMP, 8-methylthio-cAMP, $N^6$-benzoyl-cAMP, 8-bromo-cAMP, 8-iodo-cAMP, 8-p-chlorophenyl-thio-cAMP, 8-β-hydroxyethylamino-cAMP, 8-methylamino-cAMP, 8-N,N-dimethylamino-cAMP, $N^6$-phenylcarbamoyl-cAMP, $N^6$-butyryl-cAMP, $N^6,N^6$-phenyl-8-p-chlorophenylthio-cAMP, $N^6,N^6$-diethyl-8-p-chlorophenylthio-cAMP, 6-piperidino-8-p-chlorophenylthio-cAMP, $N^6$-benzyl-8-benzylthio-cAMP, $N^6$-ethoxycarbonyl-cAMP, $N^6$-n-butyl-8-p-chlorophenylthio-cAMP, pharmaceutically acceptable salts thereof, and mixtures thereof.

24. The pharmaceutical composition of claim 23, wherein said additional compound is selected from the group consisting of 8-Cl-cAMP and pharmaceutically acceptable salts thereof.

25. The pharmaceutical composition of claim 23, wherein said additional compound is selected from the group consisting of $N^6$-benzyl-cAMP and pharmaceutically acceptable salts thereof.

26. A method of inhibiting neoplastic cellular growth in a living mammal afflicted by said neoplastic cellular growth, which comprises administering a compound selected from the group consisting of phosphorothioate derivatives of cAMP analogues, wherein said cAMP analogues have been modified at either or both the $N^6$ or C-8 positions of the adenine moiety, wherein said $N^6$- or C-6 substitution is selected from the group consisting of monobenzyl, monoethoxycarbonyl, monobenzoyl, monophenylcarbamoyl, monobutyryl, monophenyl, and diethyl or N-piperidino, and wherein said C-8 substituent is selected from the group consisting of halogen, methylthio, p-chlorophenylthio, β-hydroxyethylamino and methylamino, and pharmaceutically acceptable salts thereof, in an amount sufficient to provide a serum concentration of about 0.1 to about 100 μM in said mammal and inhibit said neoplastic cellular growth in said mammal.

27. The method of claim 26, wherein said phosphorothioate derivative is modified at both the $N^6$ and C-8 positions of the adenine moiety with substituents selected from the group consisting of $N^6$-phenyl-8-p-chlorophenylthio, $N^6$, $N^6$-diethyl-8-p-chlorophenylthio, 6-piperidino-8-p-chlorophenylthio, $N^6$-benzyl-8- benzylthio, and $N^6$-(n-butyl)-8-p-chlorophenylthio.

28. A method according to claim 26 further comprising administering to a mammal 8-Cl-cAMP in admixture with a compound selected from the group consisting of $N^6$-phenyl-8-p-chlorophenylthio-cAMPS, $N^6,N^6$-diethyl-8-p-chlorophenylthio-cAMPS, 6-piperidino-8-p-chlorophenylthio-cAMPS, $N^6$-benzyl-8- benzylthio-cAMPS, and $N^6$-(n-butyl)-8-p-chlorophenylthio-cAMPS.

29. The method of claim 26, wherein said cAMP analogues are modified with a halo, thio, primary amino, secondary amino, or tertiary amino moiety.

30. The method of claim 26, wherein said phosphorothioate derivative is modified at the C-8 position of the adenine moiety with a substituent selected from the group consisting of chloro, methylthio, bromo, iodo, p-chlorophenylthio, β-hydroxyethylamino, and methylamino.

31. The method of claim 26, wherein said phosphorothioate derivative is modified at the $N^6$ position of the adenine moiety with a substituent selected from the group consisting of $N^6$-benzyl, $N^6$-ethoxycarbonyl, $N^6$-benzoyl, and $N^6$-phenyl-carbamoyl.

32. The method of claim 26, wherein said neoplastic cellular growth is breast cancer.

33. The method of claim 26, wherein said phosphorothioate derivative of cAMP is modified at the C-8 position of the adenine moiety with a halogen.

34. The method of claim 33, wherein said phosphorothioate derivative of cAMP is Rp-8-Cl-cAMPS or Sp-8-Br-cAMPS.

35. The method of claim 26, where in said mammal is a human.

36. The method of claim 35, wherein said neoplastic cellular growth is leukemia.

37. The method of claim 35, wherein said neoplastic cellular growth is colon cancer.

* * * * *